(12) United States Patent
Birgisdottir et al.

(10) Patent No.: US 10,828,179 B2
(45) Date of Patent: Nov. 10, 2020

(54) ADJUSTABLE SEAL SYSTEM, SEAL COMPONENT AND METHOD FOR USING THE SAME

(71) Applicant: Ossur Iceland ehf, Reykjavik (IS)

(72) Inventors: Linda Ros Birgisdottir, Reykjavik (IS); Martin Lund Størup, Reykjavik (IS); Johan Olof Westlund, Reykjavik (IS); Egill Sveinbjorn Egilsson, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 125 days.

(21) Appl. No.: 15/976,185

(22) Filed: May 10, 2018

(65) Prior Publication Data

US 2018/0256373 A1 Sep. 13, 2018

Related U.S. Application Data

(63) Continuation of application No. 15/480,452, filed on Apr. 6, 2017, now Pat. No. 10,322,016, which is a
(Continued)

(51) Int. Cl.
*A61F 2/78* (2006.01)
*A61F 2/80* (2006.01)
(Continued)

(52) U.S. Cl.
CPC ............ *A61F 2/7812* (2013.01); *A41F 13/00* (2013.01); *A61F 2/80* (2013.01); *A41D 13/065* (2013.01);
(Continued)

(58) Field of Classification Search
CPC ............ A61F 2/7843; A61F 2002/7818; A61F 2002/7837; A61F 2002/802; A61F 2002/805; A61F 2002/807
(Continued)

(56) References Cited

U.S. PATENT DOCUMENTS

| 980,457 A | 1/1911 | Toles |
| 1,398,824 A | 11/1921 | Abrams |

(Continued)

FOREIGN PATENT DOCUMENTS

| AT | 369 978 B | 2/1983 |
| DE | 484 363 C | 10/1929 |

(Continued)

OTHER PUBLICATIONS

International Search Report and Written Opinion from PCT Application No. PCT/US2018/058624, dated Feb. 11, 2019.
(Continued)

*Primary Examiner* — David H Willse
(74) *Attorney, Agent, or Firm* — Workman Nydegger

(57) ABSTRACT

An adjustable seal system, seal component for use in the system, and method are provided for forming a sealing interface between a residual limb and a prosthetic socket. The seal component is selectively placed over the outer surface of a suspension liner including a plurality of seal bands, which the seal component may removably and securely engage.

15 Claims, 19 Drawing Sheets

Related U.S. Application Data continuation-in-part of application No. 14/608,436, filed on Jan. 29, 2015, now Pat. No. 9,707,106, which is a continuation of application No. 14/541,505, filed on Nov. 14, 2014, now Pat. No. 9,877,851.

(60) Provisional application No. 61/946,363, filed on Feb. 28, 2014, provisional application No. 61/904,580, filed on Nov. 15, 2013.

(51) Int. Cl.
  *A41F 13/00* (2006.01)
  *A41D 13/06* (2006.01)
  *A61F 2/50* (2006.01)

(52) U.S. Cl.
  CPC .. *A41D 2400/80* (2013.01); *A61F 2002/5007* (2013.01); *A61F 2002/5021* (2013.01); *A61F 2002/5083* (2013.01); *A61F 2002/785* (2013.01); *A61F 2002/7818* (2013.01); *A61F 2002/7837* (2013.01); *A61F 2002/7868* (2013.01); *A61F 2002/802* (2013.01); *A61F 2250/0018* (2013.01)

(58) Field of Classification Search
  USPC .............................................. 623/32, 34, 36
  See application file for complete search history.

(56) References Cited

U.S. PATENT DOCUMENTS

| | | |
|---|---|---|
| 1,893,853 A | 1/1933 | Tullis |
| 2,244,871 A | 6/1941 | Guinzburg |
| 2,325,656 A | 8/1943 | Brophy |
| 2,464,443 A | 3/1949 | Ganoe et al. |
| 2,530,285 A | 11/1950 | Catranis |
| 2,533,404 A | 12/1950 | Sharp et al. |
| 2,634,424 A | 4/1953 | O'Gorman |
| 2,671,225 A | 3/1954 | Schoene et al. |
| 2,689,351 A | 9/1954 | Schindler |
| 2,808,593 A | 10/1957 | Andersen |
| 3,393,407 A | 7/1968 | Kandel |
| 3,587,572 A | 6/1971 | Evans |
| 3,663,973 A | 5/1972 | Spence |
| 3,671,980 A | 6/1972 | Baird |
| 3,947,897 A | 4/1976 | Owens |
| 4,128,903 A | 12/1978 | Marsh et al. |
| 4,215,679 A | 8/1980 | Rustin |
| 4,311,317 A | 1/1982 | Bartels |
| 4,319,413 A | 3/1982 | Mattil |
| 4,347,204 A | 8/1982 | Takagi et al. |
| 4,474,573 A | 10/1984 | Detty |
| 4,635,626 A | 1/1987 | Lerman |
| 4,738,249 A | 4/1988 | Linman et al. |
| 4,767,735 A | 8/1988 | Ewen et al. |
| 4,885,828 A | 12/1989 | Kozlowski |
| 4,908,037 A | 3/1990 | Ross |
| 4,923,474 A | 5/1990 | Klasson et al. |
| 5,007,937 A | 4/1991 | Fishman et al. |
| 5,055,528 A | 10/1991 | Kioka et al. |
| 5,108,456 A | 4/1992 | Coonan, III |
| 5,122,583 A | 6/1992 | Ewen et al. |
| 5,139,523 A | 8/1992 | Paton et al. |
| 5,163,965 A | 11/1992 | Rasmusson et al. |
| 5,169,161 A | 12/1992 | Jones |
| 5,226,918 A | 7/1993 | Silagy et al. |
| 5,244,716 A | 9/1993 | Thornton et al. |
| 5,314,496 A | 5/1994 | Harris et al. |
| 5,376,129 A | 12/1994 | Faulkner et al. |
| 5,376,131 A | 12/1994 | Lenze et al. |
| 5,387,245 A | 2/1995 | Fay et al. |
| 5,549,709 A | 8/1996 | Caspers |
| 5,571,208 A | 11/1996 | Caspers |
| 5,571,209 A | 11/1996 | Brown, Sr. |
| 5,593,454 A | 1/1997 | Helmy |
| 5,658,353 A | 8/1997 | Layton |
| 5,702,489 A | 12/1997 | Slemker |
| 5,718,925 A | 2/1998 | Kristinsson et al. |
| 5,728,168 A | 3/1998 | Laghi et al. |
| 5,728,170 A | 3/1998 | Becker et al. |
| 5,735,906 A | 4/1998 | Caspers |
| 5,830,237 A | 11/1998 | Kania |
| 5,885,674 A | 3/1999 | Maemoto et al. |
| 5,888,216 A | 3/1999 | Haberman |
| 5,888,230 A | 3/1999 | Helmy |
| 5,904,722 A | 5/1999 | Caspers |
| 5,931,872 A | 8/1999 | Lohmann |
| 5,972,036 A | 10/1999 | Kristinsson et al. |
| 5,980,577 A | 11/1999 | Radis et al. |
| 6,076,284 A | 6/2000 | Terlizzi |
| 6,136,039 A | 10/2000 | Kristinsson et al. |
| 6,149,691 A | 11/2000 | Fay et al. |
| 6,171,431 B1 | 1/2001 | Gallagher, Jr. et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 6,361,568 B1 | 3/2002 | Hoerner |
| 6,368,357 B1 | 4/2002 | Schon et al. |
| 6,406,499 B1 | 6/2002 | Kania |
| 6,454,812 B1 | 9/2002 | Laghi |
| 6,468,938 B1 | 10/2002 | Govoni et al. |
| 6,485,776 B2 | 11/2002 | Janusson et al. |
| 6,508,842 B1 | 1/2003 | Caspers |
| 6,544,292 B1 | 4/2003 | Laghi |
| 6,554,868 B1 | 4/2003 | Caspers |
| 6,585,774 B2 | 7/2003 | Dean, Jr. et al. |
| 6,592,539 B1 * | 7/2003 | Einarsson ............. A61F 5/0109 602/26 |
| 6,626,952 B2 | 9/2003 | Janusson et al. |
| 6,645,253 B2 | 11/2003 | Caspers |
| 6,706,364 B2 | 3/2004 | Janusson et al. |
| 6,726,726 B2 | 4/2004 | Caspers |
| 6,761,742 B2 | 7/2004 | Caspers |
| 6,797,008 B1 | 9/2004 | Arbogast et al. |
| 6,852,269 B2 | 2/2005 | Eberle et al. |
| 6,926,742 B2 | 8/2005 | Caspers et al. |
| 6,929,125 B1 | 8/2005 | Seamans |
| 6,964,688 B1 | 11/2005 | Kania |
| 7,001,563 B2 | 2/2006 | Janusson et al. |
| 7,025,793 B2 | 4/2006 | Egilsson |
| 7,118,602 B2 | 10/2006 | Bjarnason |
| 7,144,429 B2 | 12/2006 | Carstens |
| 7,169,188 B2 | 1/2007 | Carstens |
| 7,169,189 B2 | 1/2007 | Bjarnason et al. |
| 7,235,108 B2 | 6/2007 | Carstens |
| 7,291,182 B1 | 11/2007 | Kania |
| 7,351,264 B2 | 4/2008 | Wilson |
| 7,427,297 B2 | 9/2008 | Patterson et al. |
| 7,592,286 B2 | 9/2009 | Morini et al. |
| 7,749,281 B2 | 7/2010 | Egilsson |
| 7,771,487 B2 | 8/2010 | Mantelmacher |
| 7,909,884 B2 | 3/2011 | Egilsson et al. |
| 8,034,120 B2 | 10/2011 | Egilsson et al. |
| 8,052,760 B2 | 11/2011 | Egilsson et al. |
| 8,097,043 B2 | 1/2012 | Egilsson |
| 8,206,459 B1 | 6/2012 | Lock et al. |
| 8,372,159 B2 | 2/2013 | Mackenzie |
| 8,894,719 B2 | 11/2014 | Egilsson et al. |
| 8,911,506 B2 | 12/2014 | Egilsson et al. |
| 9,056,022 B2 | 6/2015 | Egilsson et al. |
| 9,060,885 B2 | 6/2015 | Egilsson et al. |
| 9,066,821 B2 | 6/2015 | Egilsson et al. |
| 9,295,567 B2 | 3/2016 | Egilsson et al. |
| 9,566,175 B2 | 2/2017 | Halldorsson |
| 9,603,726 B2 | 3/2017 | Egilsson et al. |
| 9,707,106 B2 | 7/2017 | Egilsson et al. |
| 2001/0005798 A1 | 6/2001 | Caspers |
| 2001/0016781 A1 | 8/2001 | Caspers |
| 2002/0040248 A1 | 4/2002 | Karason |
| 2002/0087215 A1 | 7/2002 | Caspers |
| 2002/0091449 A1 | 7/2002 | Caspers et al. |
| 2002/0099450 A1 | 7/2002 | Dean, Jr. et al. |

(56) References Cited

U.S. PATENT DOCUMENTS

| | | |
|---|---|---|
| 2002/0165619 A1 | 11/2002 | Hellberg |
| 2002/0183859 A1 | 12/2002 | Houser |
| 2003/0181989 A1 | 9/2003 | Eberle et al. |
| 2003/0191539 A1 | 10/2003 | Caspers |
| 2004/0012158 A1 | 1/2004 | Neuhaus |
| 2004/0024322 A1 | 2/2004 | Caspers |
| 2004/0030411 A1 | 2/2004 | Caspers |
| 2004/0040248 A1 | 3/2004 | Vilnes |
| 2004/0098136 A1 | 5/2004 | Caspers |
| 2004/0122528 A1 | 6/2004 | Egilsson |
| 2004/0143345 A1 | 7/2004 | Caspers |
| 2004/0167638 A1 | 8/2004 | Caspers |
| 2004/0181290 A1 | 9/2004 | Caspers |
| 2004/0236434 A1 | 11/2004 | Carstens |
| 2004/0243251 A1 | 12/2004 | Carstens |
| 2004/0243252 A1 | 12/2004 | Carstens |
| 2005/0101693 A1 | 5/2005 | Arbogast et al. |
| 2005/0216095 A1 | 9/2005 | Egilsson |
| 2005/0240282 A1 | 10/2005 | Rush et al. |
| 2005/0240283 A1 | 10/2005 | Kania |
| 2005/0267598 A1 | 12/2005 | Bjarnason et al. |
| 2005/0267599 A1* | 12/2005 | Bjarnason ............. A61F 2/7812 623/36 |
| 2006/0212128 A1 | 9/2006 | Nachbar |
| 2006/0293762 A1 | 12/2006 | Schulman et al. |
| 2007/0005149 A1 | 1/2007 | Egilsson et al. |
| 2007/0021295 A1 | 1/2007 | Morini et al. |
| 2007/0027556 A1 | 2/2007 | Wilson |
| 2007/0043450 A1 | 2/2007 | Pickering et al. |
| 2007/0061017 A1 | 3/2007 | Wilson |
| 2007/0123998 A1 | 5/2007 | Egilsson et al. |
| 2007/0179606 A1 | 8/2007 | Huyghe et al. |
| 2008/0086218 A1 | 4/2008 | Egilsson |
| 2008/0147202 A1 | 6/2008 | Danzig et al. |
| 2008/0188949 A1 | 8/2008 | Mackenzie |
| 2008/0221705 A1 | 9/2008 | Scussel |
| 2008/0221706 A1 | 9/2008 | Scussel et al. |
| 2008/0269914 A1 | 10/2008 | Coppens et al. |
| 2009/0036999 A1 | 2/2009 | Egilsson et al. |
| 2009/0069171 A1 | 3/2009 | Sagae |
| 2009/0157196 A1 | 6/2009 | Danzig et al. |
| 2009/0182435 A1 | 7/2009 | Haberman |
| 2009/0198346 A1 | 8/2009 | Perkins et al. |
| 2009/0240344 A1 | 9/2009 | Colvin et al. |
| 2009/0306791 A1 | 12/2009 | Slemker et al. |
| 2010/0070051 A1 | 3/2010 | Carstens |
| 2010/0185300 A1 | 7/2010 | Mackenzie |
| 2010/0249950 A1 | 9/2010 | Bielefeld |
| 2010/0274364 A1 | 10/2010 | Pacanowsky et al. |
| 2010/0318196 A1 | 12/2010 | Egilsson |
| 2011/0029096 A1 | 2/2011 | Laghi |
| 2011/0035027 A1 | 2/2011 | Mccarthy |
| 2011/0054635 A1 | 3/2011 | Watts |
| 2011/0071649 A1 | 3/2011 | Mckinney |
| 2011/0077748 A1 | 3/2011 | Egilsson et al. |
| 2011/0118854 A1 | 5/2011 | Halldorsson |
| 2012/0041568 A1 | 2/2012 | Mackenzie |
| 2012/0095571 A1 | 4/2012 | Gunnarsson et al. |
| 2013/0053982 A1 | 2/2013 | Halldorsson |
| 2013/0138224 A1 | 5/2013 | Mackenzie |
| 2013/0197670 A1 | 8/2013 | Mackenzie |
| 2013/0331952 A1 | 12/2013 | Halldorsson et al. |
| 2015/0142133 A1 | 5/2015 | Egilsson et al. |
| 2015/0202060 A1 | 7/2015 | Muller et al. |
| 2016/0106557 A1 | 4/2016 | Egilsson et al. |
| 2017/0105853 A1 | 4/2017 | Jonsson et al. |
| 2017/0151073 A1 | 6/2017 | Halldorsson |
| 2017/0209290 A1 | 7/2017 | Birgisdottir et al. |
| 2017/0304085 A1 | 10/2017 | Kurth |

FOREIGN PATENT DOCUMENTS

| | | |
|---|---|---|
| DE | 745 981 C | 5/1944 |
| DE | 813 190 C | 9/1951 |
| DE | 1 795 809 U | 9/1959 |
| DE | 2 060 239 A1 | 6/1972 |
| DE | 2 127 269 A1 | 12/1972 |
| DE | 2 540 138 A1 | 3/1977 |
| DE | 2 544 446 A1 | 4/1977 |
| DE | 3 221 920 A1 | 4/1983 |
| DE | 3 508 919 A1 | 9/1986 |
| DE | 9 419 208 U1 | 1/1995 |
| EP | 0 631 765 A1 | 1/1995 |
| EP | 2353550 A1 | 8/2011 |
| EP | 2745807 A1 | 6/2014 |
| EP | 2815728 A1 | 12/2014 |
| FR | 2 420 335 A1 | 10/1979 |
| FR | 2 539 616 A1 | 7/1984 |
| FR | 2 828 093 A1 | 2/2003 |
| GB | 263 377 A | 12/1926 |
| GB | 267 988 A | 3/1927 |
| GB | 826 041 A | 12/1959 |
| GB | 2 069 847 A | 9/1981 |
| GB | 2 087 727 A | 6/1982 |
| JP | H0623406 A | 2/1994 |
| JP | H07109314 A | 4/1995 |
| JP | H7-155343 A | 6/1995 |
| JP | H9-104714 A | 4/1997 |
| JP | 2637076 B2 | 8/1997 |
| JP | 2740503 B2 | 4/1998 |
| JP | H10-182740 A | 7/1998 |
| JP | 2001-055413 A | 2/2001 |
| JP | 2002-500697 A | 1/2002 |
| JP | 2006-176565 A | 7/2006 |
| JP | 2006-316160 A | 11/2006 |
| JP | 2006-528271 A | 12/2006 |
| JP | 3984304 B2 | 10/2007 |
| JP | 2011206118 A | 10/2011 |
| WO | 97/34548 A2 | 9/1997 |
| WO | 00/74611 A2 | 12/2000 |
| WO | 01/54631 A1 | 8/2001 |
| WO | 01/67842 A1 | 9/2001 |
| WO | 02/26158 A2 | 4/2002 |
| WO | 03/024367 A2 | 3/2003 |
| WO | 03/024370 A1 | 3/2003 |
| WO | 03/039398 A2 | 5/2003 |
| WO | 03/099173 A1 | 12/2003 |
| WO | 2004/060136 A2 | 7/2004 |
| WO | 2010/085336 A1 | 7/2010 |
| WO | 2013/005735 A1 | 1/2013 |
| WO | 2015073793 A1 | 5/2015 |

OTHER PUBLICATIONS

International Search Report from PCT Application No. PCT/US2017/029063, dated Jul. 21, 2017.

Extended European Search Report from EP Application No. 17198627.6, dated Jan. 29, 2018.

"Silicone-Only Suspension (SOS) with Socket-Loc and the Ring for the Lower Limb," found at, http://www.oandp.org/ipo/library/1995_01_002.asp. Journal of Prosthetics and Orthotics 1995;vol. 7, No. 1, p. 2.

Iceross Comfort Locking/Cushion Product Information Brochure, Mar. 27, 2009, 3 Pages.

Iceross Dermo, Product Information Sheets from Internet, http://www.ossur.com/prosthetics/liners/dermo, Mar. 27, 2009, 2 Sheets.

Military inStep: Prosthetic Socks and Liners, Product Information Sheets from Internet, http://www.amputee-coalition.org/military-instep/prosthetic-socks, Mar. 27, 2009, 3 Pages.

Prosthetic & Orthotic Update NewsLetter, No. 32, Internet Search Conducted Mar. 27, 2009, 4 Pages.

Walopur Platilon U, Product Information Brochure of Epurex Films GmbH & Co., KG, Internet Search Result Conducted Mar. 27,2009, 2 Pages.

International Search Report and Written Opinion Issued in PCT/US2012/051645, dated Dec. 3, 2012.

Supplementary EP Search Report from EP Application No. 07837275.2, dated Feb. 19, 2014, 6 pages.

Extended European Search Report from EP Application No. 14161004.8, dated May 22, 2014, 6 pages.

(56) References Cited

OTHER PUBLICATIONS

Extended European Search Report from Corresponding Application No. 14163512.8, dated Jul. 30, 2014.
ESP Opti-Seal, Product Installation Instructions, http://www.wearesp.com, Downloaded Dec. 12, 2014, 1 page.
ESP Opti-Seal, "The Most Versatile Suspension System Availiable," www.wearesp.com, Downloaded Dec. 12, 2014, 2 pages.
ESP Secure-Ring System (SRS), http://www.wearesp.com, Downloaded Dec. 12, 2014, 1 page.
ESP Secure-Ring System (SRS), Product Instructions Sheet, http://www.wearesp.com, downloaded Dec. 12, 2014, 2 pages.
International Search Report from PCT Application No. PCT/US2016/055269, dated Jan. 4, 2017.
Eshraghi et al., "Gait Biomechanics of Individuals with Transtibial Amputation: Effect of Suspension System," PLOS ONE, vol. 9, Issue. 5, May 2014, 12 Pages.
Eshraghi et al., "Pistoning Assessment in Lower Limb Prosthetic Sockets," Prosthetics and Orthotics International, vol. 36, No. 1, 2012, pp. 15-24.
Gholizadeh et al., "Transtibial Prosthesis Suspension Systems: Systematic Review of Literature," Clinical Biomechanics vol. 29, 2014, pp. 87-97.
"Slick SIL LSR," Surface Solutions Group LLC, retrieved from www.surfacesolutionsgroup.com on Mar. 30, 2017, 1 Page.
"Prosthetics Product Catalogue", Medi Prosthetics, www.medi-prosthetics.com, Jan. 2016, 184 pages.
"Verwendung und Verklebung Des LITE Vakuum-Ringes 5W700: Usage and Gluing of the 5W700 LITE Vacuum Ring," Wagner Polymertechnik GMBH, Sep. 6, 2016, 4 Pages.

\* cited by examiner

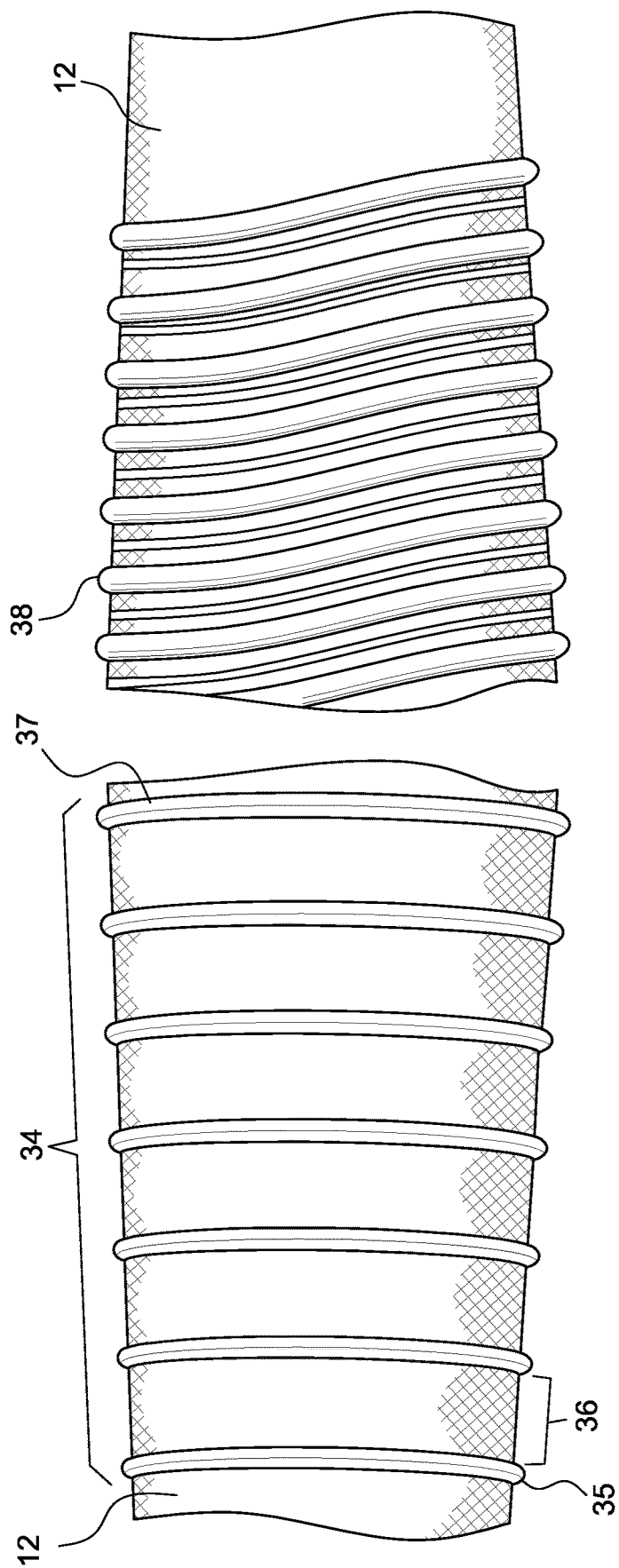

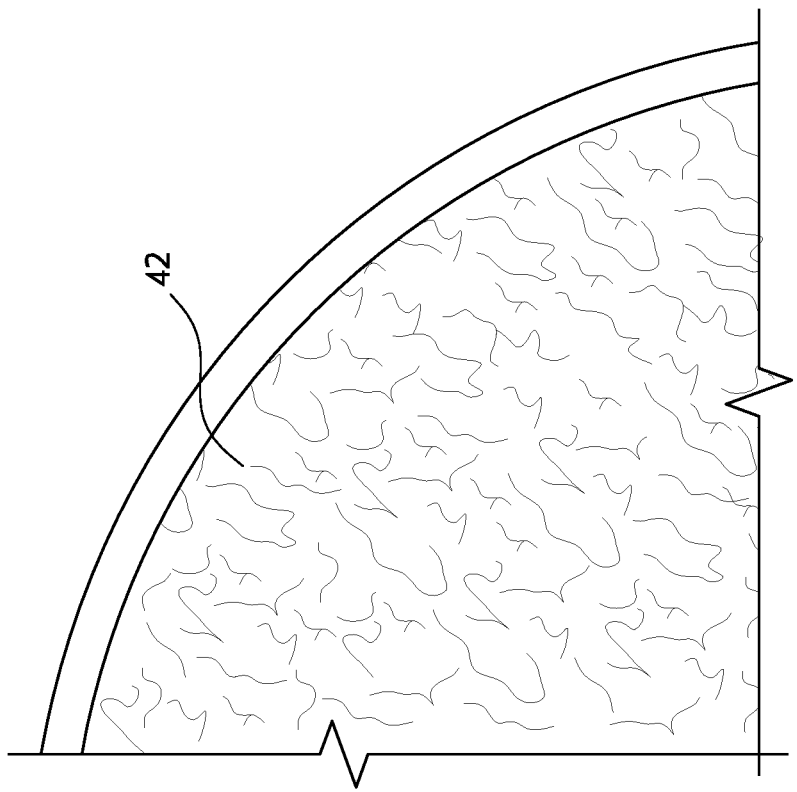
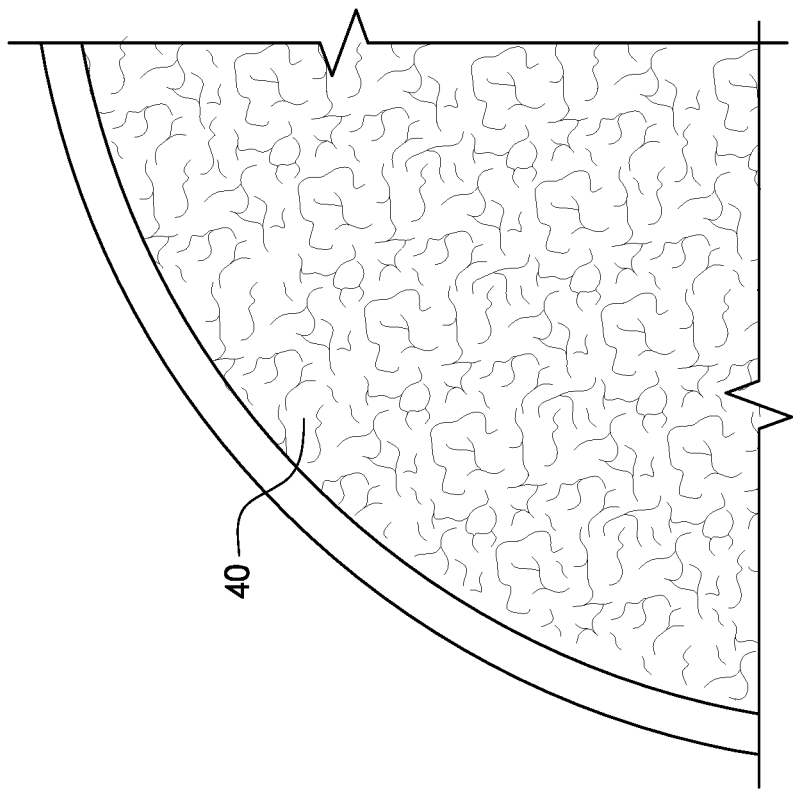

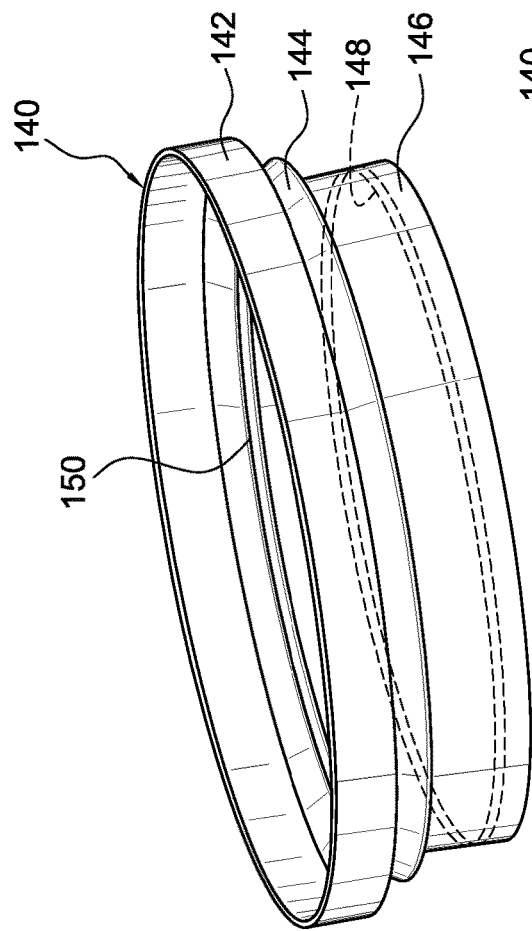
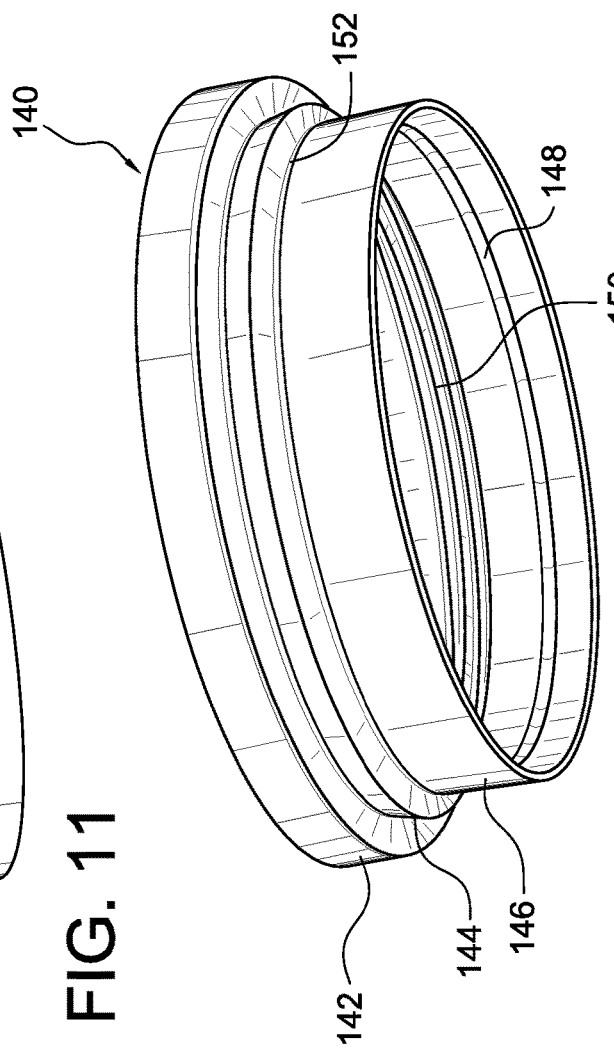
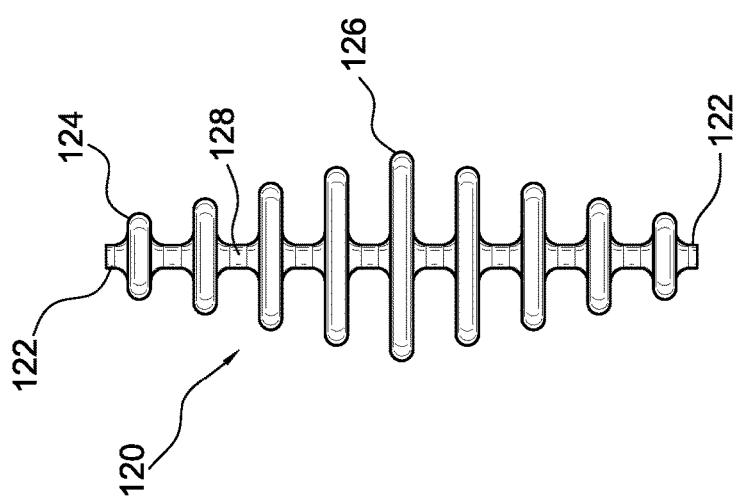

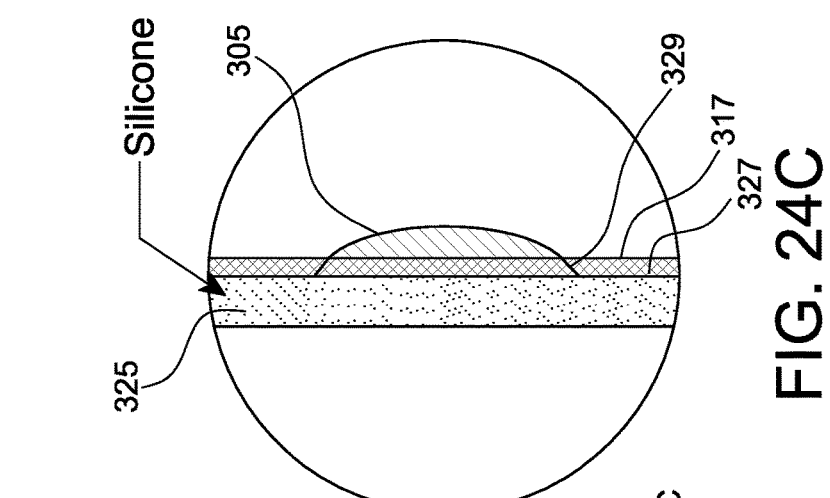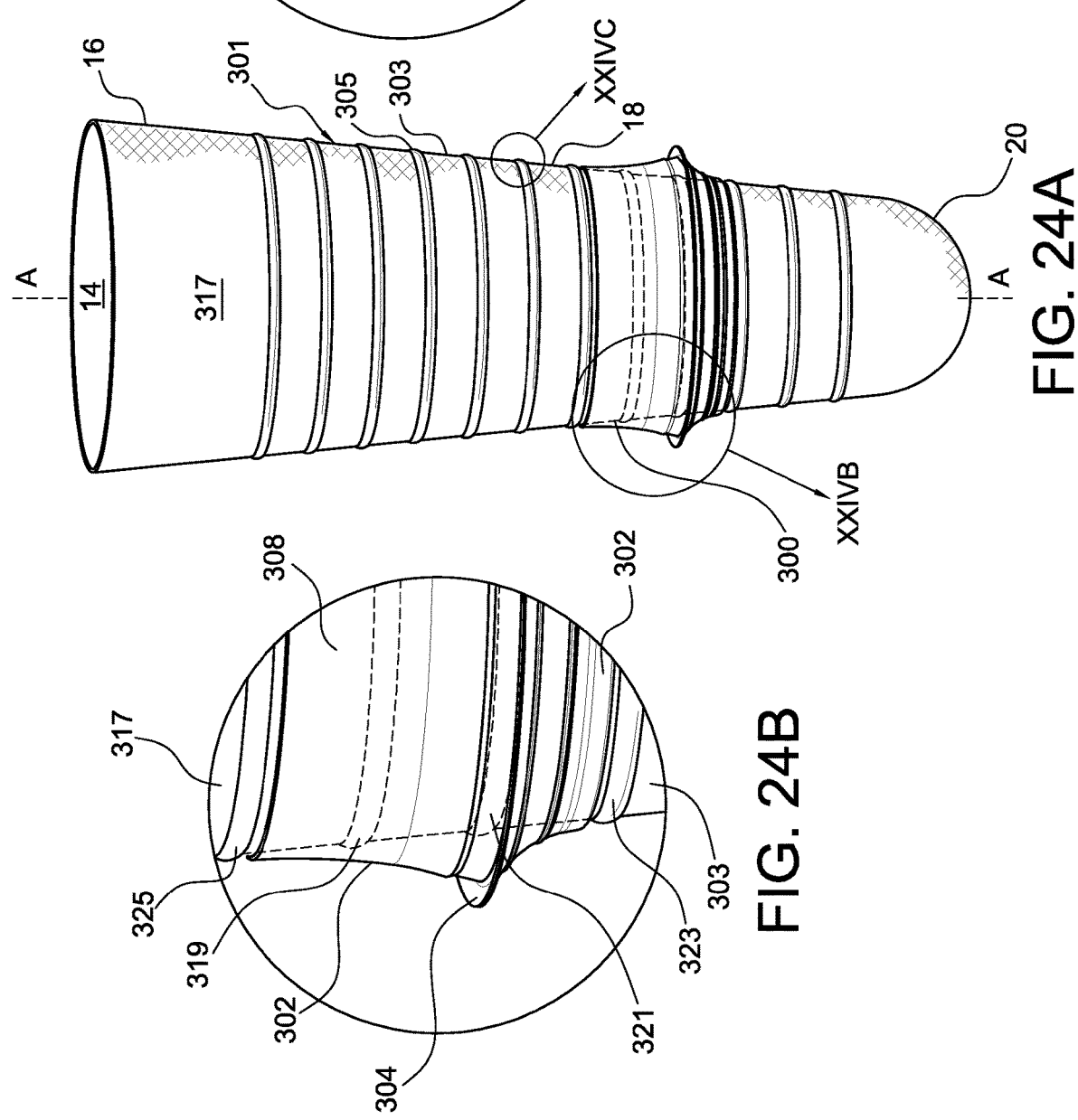

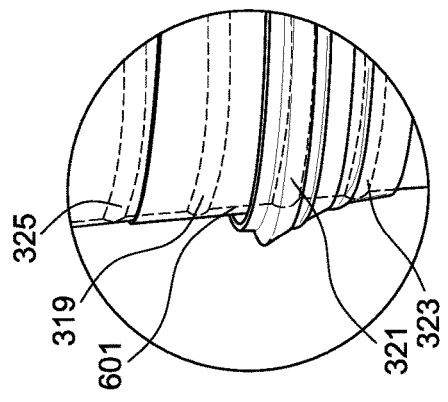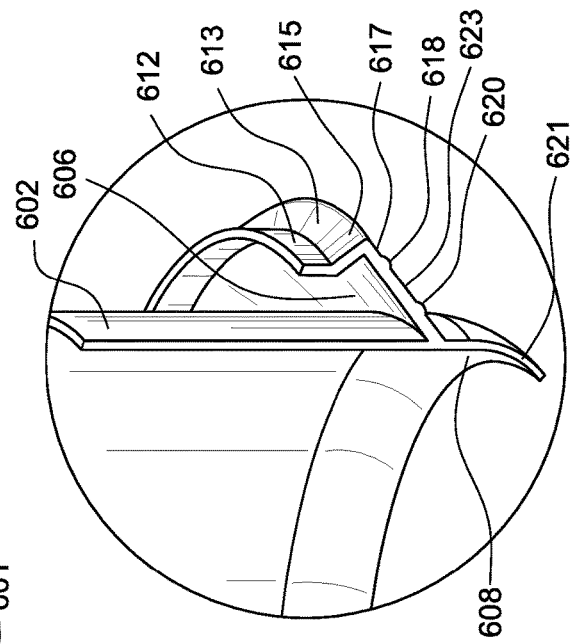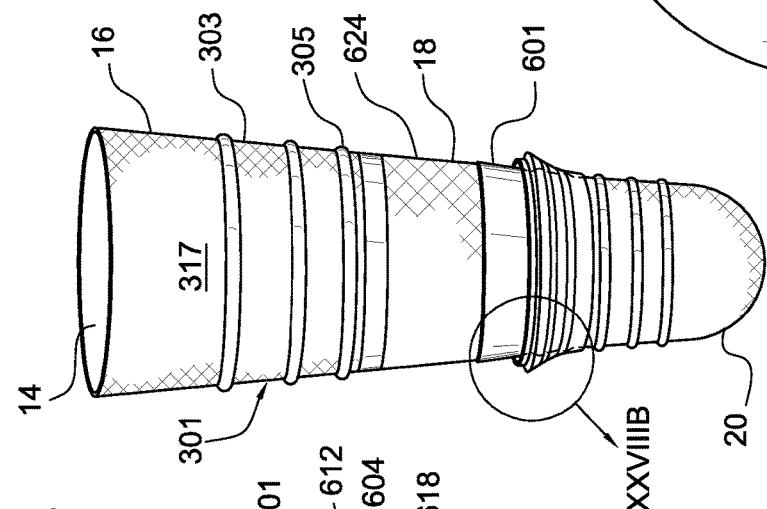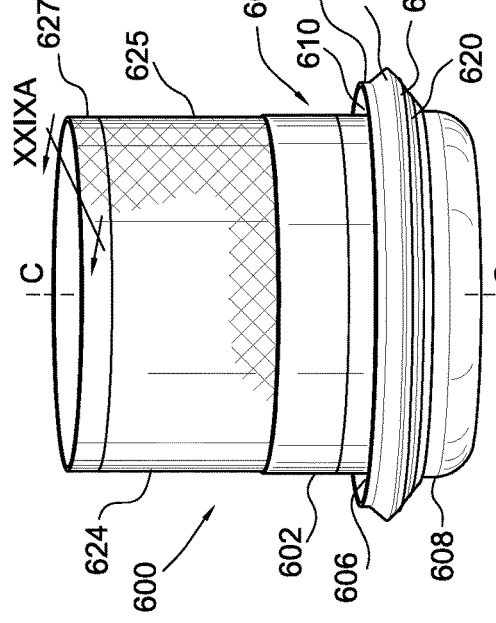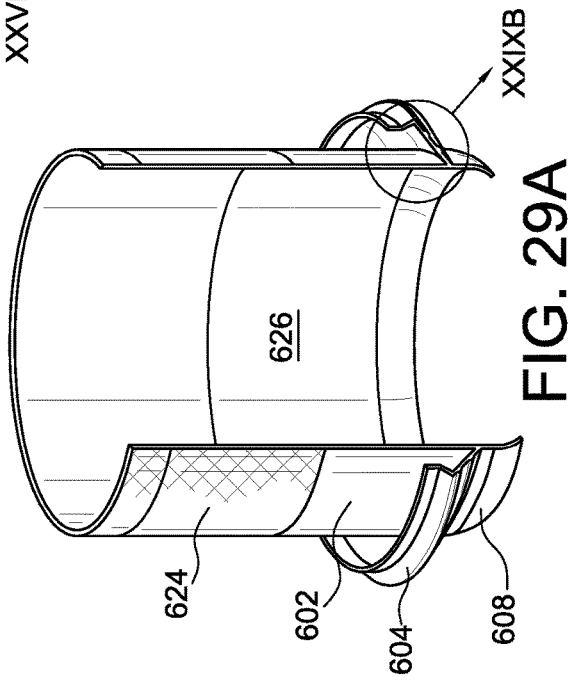

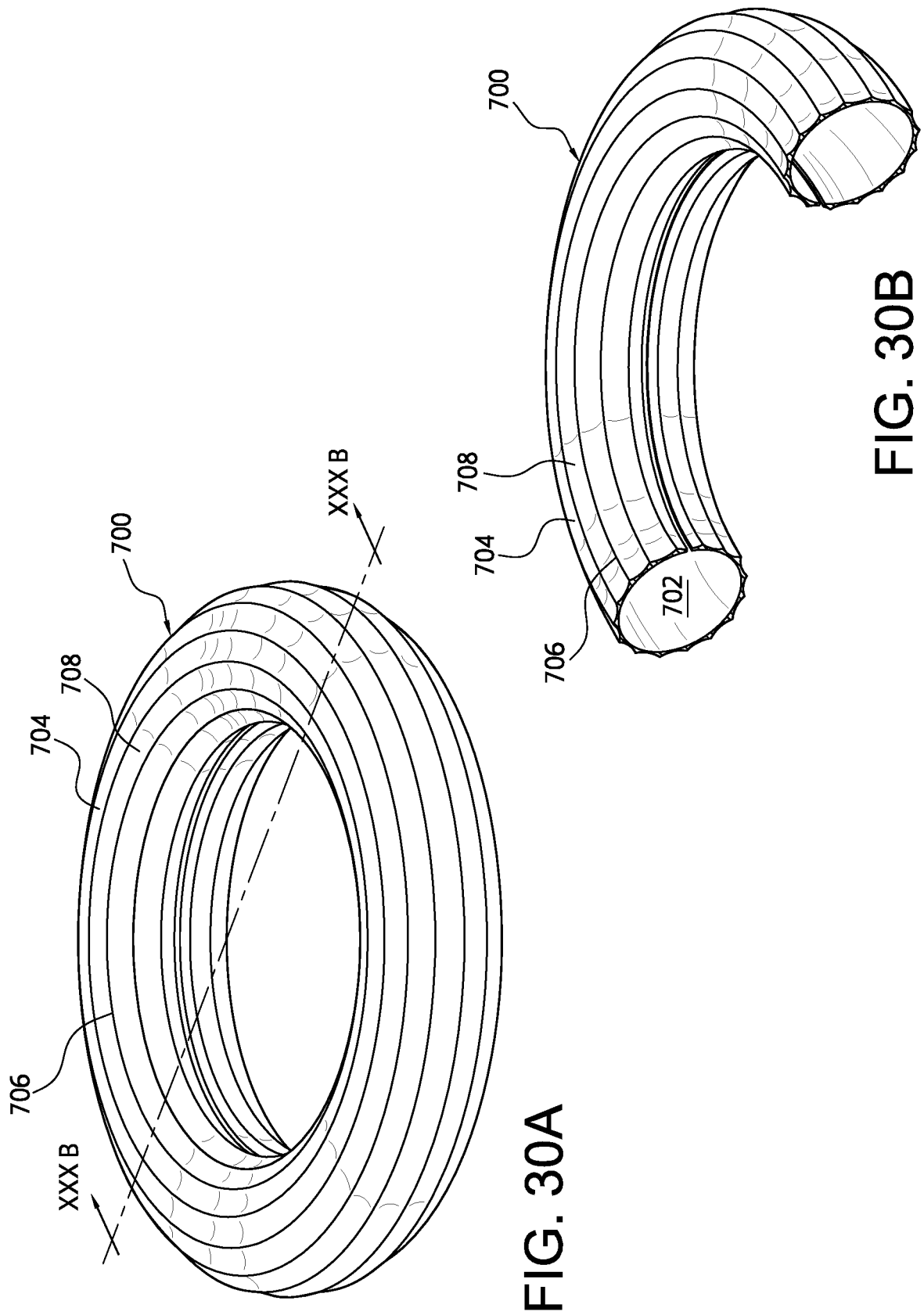

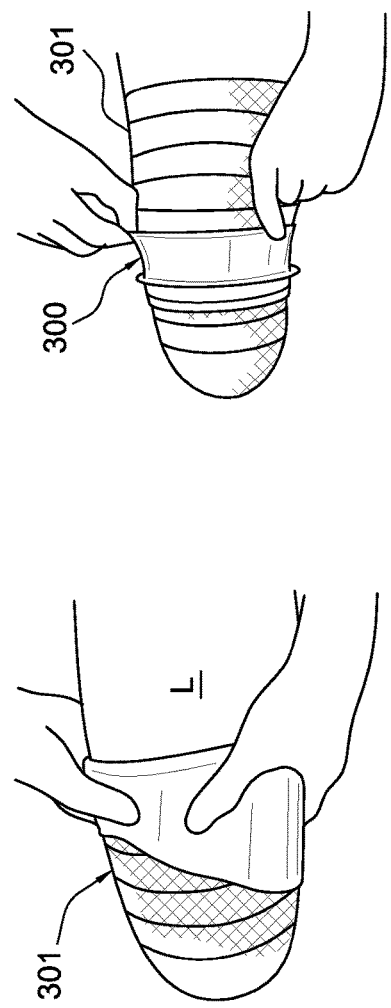
FIG. 31A
FIG. 31B
FIG. 31C
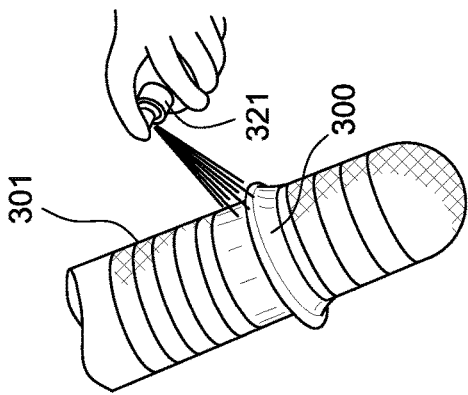
FIG. 31D
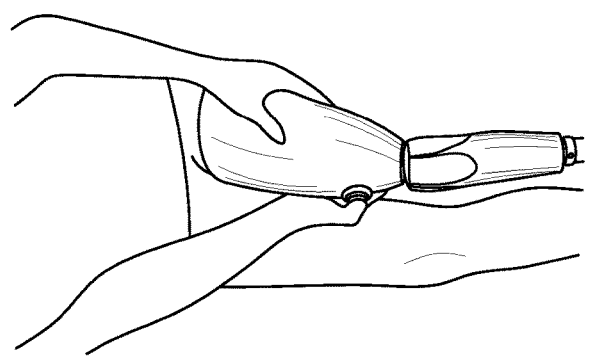
FIG. 31E

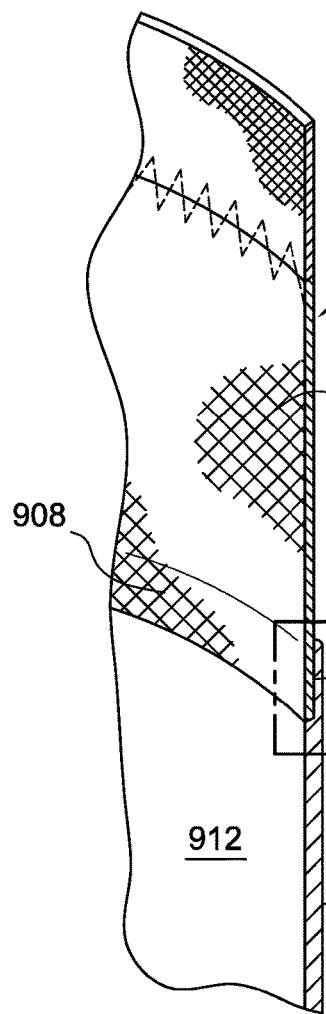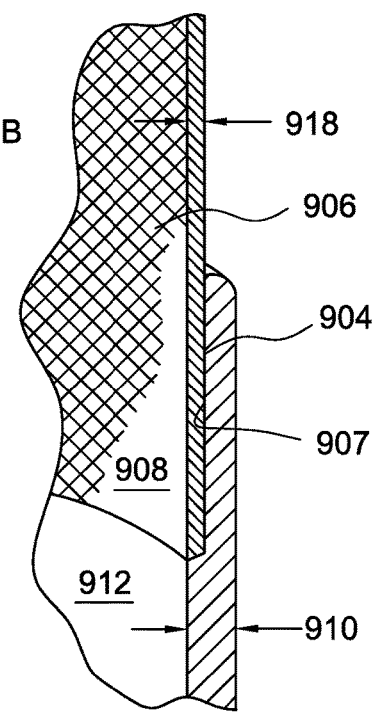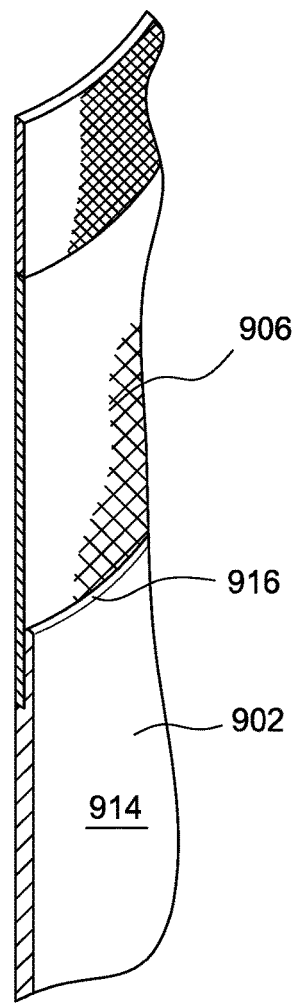
FIG. 36A  FIG. 36B  FIG. 36C
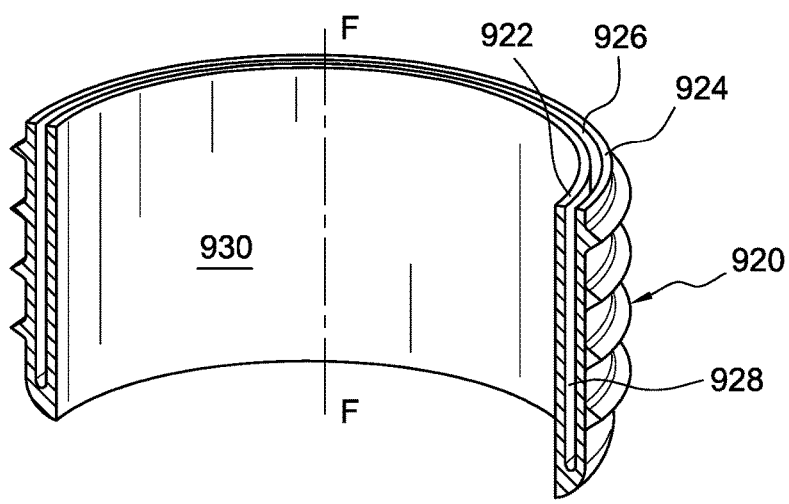
FIG. 37

ADJUSTABLE SEAL SYSTEM, SEAL COMPONENT AND METHOD FOR USING THE SAME

CROSS REFERENCE TO RELATED APPLICATIONS

This application is a continuation of U.S. application Ser. No. 15/480,452, filed Apr. 6, 2017, now U.S. Pat. No. 10,322,016, which is a continuation-in-part of U.S. application Ser. No. 14/608,436, filed Jan. 29, 2015, now U.S. Pat. No. 9,707,106, which is a continuation of U.S. patent application Ser. No. 14/541,505, filed Nov. 14, 2014, now U.S. Pat. No. 9,877,851, which claims the benefit of priority from U.S. provisional application Ser. No. 61/946,363, filed Feb. 28, 2014, and 61/904,580, filed Nov. 15, 2013, wherein each of the aforementioned priority applications are incorporated herein by reference.

This application incorporates by reference the following U.S. patent applications and patents: U.S. application Ser. No. 13/179,896, filed on Jul. 11, 2011, which is a continuation of U.S. patent application Ser. No. 11/654,549, filed on Jan. 18, 2007, now U.S. Pat. No. 8,034,120, which is a continuation-in-part of U.S. patent application Ser. No. 11/516,500, filed on Sep. 7, 2006, now U.S. Pat. No. 7,909,884, which is a continuation-in-part of U.S. patent application Ser. No. 11/135,354 filed on May 24, 2005, now U.S. Pat. No. 7,749,281, which is a divisional application of U.S. patent application Ser. No. 10/690,545 filed on Oct. 23, 2003, now U.S. Pat. No. 7,025,793, which claims the benefit of priority from U.S. provisional application 60/434,669 filed on Dec. 20, 2002. U.S. patent application publication 2013/0053982, published on Feb. 28, 2013 is also incorporated by reference in its entirety.

BACKGROUND

A. Field of the Disclosure

This disclosure relates to suspension liners adapted to provide an interface between a residual limb and a prosthetic socket. The disclosure provides various embodiments of an adjustable seal system, seal components for use in the system, and methods for providing a sealing interface between a residual limb and a prosthetic socket.

B. Discussion of Related Art

Suspension liners provide a soft, flexible interface between a residual limb of an amputee and a hard socket to which a prosthetic device is secured. Such liners are known in the art generally, as exemplified by U.S. Pat. No. 4,923,474 granted May 8, 1990 to Klasson and Kristinsson. These liners are typically made of an air impermeable elastomer material such as silicone and may include a reinforcement layer intermediate the inner and outer surfaces of the liner body portion or externally thereof to provide resistance against axial elongation of the elastomer constituting the liner body. Such reinforcement typically does not restrict radial distension or stretching of the liner body.

The liners may also include an outer covering different from the elastomeric material, and exemplary outer coverings include various textiles having different stretchability properties. For example, the outer cover may be a strong and stretchable nylon outer cover providing resistance to extreme wear and tear, and affording strength and durability. The nylon outer cover may be used to increase radial stretch and comfortable elasticity.

In the prior art, liners may function to secure the residual limb within a prosthetic socket once the residual limb and sleeve are inserted into the socket in close-fitting relationship by isolating the distal end area of the hard socket from the atmosphere. Upon application of a pulling force on the liner relative to the socket, suction is created in the distal end of the socket tending to retain the liner within the socket. Appropriate devices are usually provided to enable expulsion of air between the distal end of the liner and the hard socket, and to isolate the distal end of the hard socket member from the atmosphere after the liner with a residual limb has been fully inserted within the socket member.

In some applications, the liner is provided with an umbrella at its distal end and a threaded socket for receiving a prosthetic securing pin member which then extends through an axial opening in the distal end of the hard socket member for securing the socket member relative to a prosthetic device mounted to the distal end of the socket member. In other applications, the prosthetic device is secured to the exterior of the distal end of the hard socket member and the sleeve member is fully contained within the hard socket member.

The elastomer constituting the liner may be arranged to frictionally engage and remain attached to the skin of a residual limb so that the limb is retained within the hard socket member in a comfortable, non-irritating manner. The liner may be thickened to provide cushioning effect between the residual limb and the hard socket, which is typically custom made to closely fit the residual limb. Liners of this kind are used for both trans-tibial (TT) amputees as well as trans-femoral (TF) amputees. That is, the liners may be utilized for applications above the knee or below the knee of the amputee.

In other applications, it may be desired to more positively secure the liner within the socket by creating a hypobaric (vacuum) pressure within the distal end of the hard socket between such distal end and the distal end of a liner inserted into the socket with a residual limb contained within the liner. The hypobaric pressure may be maintained at the distal end of the hard socket and the interior of the socket at its distal end will be isolated from atmosphere during normal retention of the sleeve liner within the socket. Opening the distal end of the socket to atmosphere releases the vacuum or hypobaric pressure within the socket to enable simple withdrawal of a residual limb with a liner thereon from the socket.

A pump or other device may be utilized to evacuate the distal end of the socket between the distal end of a liner and the distal end of a socket. A valve or other appropriate device typically is used to open and close the distal end of a socket to surrounding atmosphere.

Various arrangements are known in the prior art for providing an appropriate seal between the exterior of the liner and the interior of the hard socket including external air impermeable sleeves covering the interface area between the proximal end of the hard socket and the adjacent liner body.

In trans-femoral applications, the sealing between a sleeve and a socket is generally simpler and easier to execute than sealing a trans-tibial liner against the inner surface of a socket because in the latter situation, the residual limb contains more bony protuberances and irregular shapes that are difficult to effectively seal, particularly if it is desired to simply use the material of the elastomeric liner as the sealing element.

Some users find that known liners having sealing means fail to sufficiently tolerate volume fluctuations, and may leave pressure marks on the residual limb after periods of sustained use. Additional improvements may be required for some users in that known liners do not adequately conform to the user's anatomy, and therefore fail to provide necessary comfort and skin protection. Moreover, as with all suspension liners having sealing means, it is necessary that the liner provides reliable suspension after an initial phase of volume and shape conditioning after the liner is donned on the user's residual limb.

SUMMARY

The disclosure provides various embodiments of an adjustable seal system, seal components for use in the system, and methods for providing a sealing interface between a residual limb and a prosthetic socket. The embodiments are beneficial to address the challenges faced by amputees by providing flexibility in placement of a seal component to avoid various pressure points and accommodate the shape of the residual limb.

According to an embodiment, the adjustable seal system includes a suspension liner defining a liner body forming an axis and having an outer surface including a plurality of seal bands located along the height of the liner body. A seal component has open upper and lower ends defining an opening therethrough and an internal surface having an axis arranged concentric with the axis of the liner body. The internal surface is arranged to frictionally engage at least one of the plurality of seal bands and secure on the outer surface of the liner body.

The liner preferably defines a closed-ended distal portion and the seal component is adapted to be inserted onto the liner from the distal portion. The liner defines an open-ended proximal portion and the proximal portion preferably has a greater diameter than the distal portion. Alternatively, the liner may have a consistent diameter above the distal portion, and along middle and proximal portions of the liner. A diameter of the opening of the seal component may be less than the diameter of the proximal portion.

The at least one seal band may be formed from a polymeric material and the outer surface of the liner body may be defined by a textile-based cover. The at least one seal band may be formed so as to bleed or wet through a textile of the textile-based cover and interlock therewith.

In an embodiment of the seal component, an upper portion may have a segment with a curvature descending to a seal. A lower portion may have a segment curvingly ascending to the seal. The seal may extend from the lower portion and a distance beyond the periphery of the curvature. The upper portion may define a recess formed by the periphery of the curvature proximate the seal. A bevel preferably delimits a top portion of the recess from the curvature. The lower portion may define a plurality of seal bands circumferentially extending around the periphery of the lower portion. The seal bands may be arranged along the height of the lower portion.

The seal may be arranged to protrude away from the outer surface of the liner body. The seal may be arranged to collapse against the outer surface when placed and engaging a socket, essentially losing the distance.

The seal may form a flap protruding away from an upper portion of the seal component a predetermined distance while having a base intersecting with the upper curvature. The upper portion may define a recess formed by the periphery of the curvature proximate the seal. A bevel may delimit a top portion of the recess from the curvature. The flap generally has a size corresponding to the recess such that upon insertion into a socket, the flap is urged into the recess, and has an end portion abutting the bevel. The upper and lower portions generally intersect at a base of the flap.

The seal component may define interior blades located along the interior surface and correspond in location to the seal located on the exterior side of the seal component. The interior blades may be arranged in a variety of different formations, and are preferably at an angle oriented obliquely relative to the axis of the seal component.

The seal component is not limited to the embodiments discussed above but may be arranged in a variety of configurations with an interior arrangement to secure against a liner body of a suspension liner and an exterior arrangement to secure against a surface of a socket for providing a sealing interface between a residual limb and a prosthetic socket.

The adjustable seal system may include a textile sleeve secured to an upper portion of the seal component and arranged to radially compress against the outer surface of the liner. The textile sleeve is preferably an anatomical conforming fabric. The textile provides an interface for gripping, and thereby minimizing fine hand movements needed to don and adjust the seal component over the liner. The sleeve is preferably more flexible and elastic than the seal component such that the sleeve retracts to an original size upon release of tension of the sleeve. The sleeve has a diameter less than a diameter of the liner body at the distal portion such that the sleeve stretches over and is tensioned when selectively placed over the outer surface of the liner body. The sleeve includes a main portion having a first elasticity, and a top band located at an upper end of the main portion and having a second elasticity.

Whether alone or in combination with the textile sleeve, the seal component may define a body forming an interior surface arranged to span a distance between at least two seal bands and engage therewith. A seal may be located below an upper portion and above a lower portion wherein the upper portion is generally concentric with the liner body and the seal protrudes radially outwardly from the axis relative to the upper portion. The seal may have a radially outermost portion arranged generally concentric with the upper portion. The seal may have a lower segment extending outwardly from the lower portion to the radially outermost portion.

The seal may have an upper segment extending inwardly from the radially outermost portion toward the upper portion. A clearance is defined between the upper portion and the upper segment such that the seal is arranged to be compressed against the upper portion. The seal can define a flap extending from the upper segment. The flap is arranged generally parallel with the upper portion and spaced from the upper portion by the clearance.

The seal component includes a seal located below an upper portion and above a lower portion. The seal has a lower segment extending outwardly from the lower portion to a radially outermost portion and at least one radial seal projecting outwardly from the lower segment. The seal component includes a seal located below an upper portion and above a lower portion and having a radially outermost portion spaced by a clearance from the upper portion. The seal component has a lower portion defining a curvature and an upper portion having a substantially uniform diameter along its height. The lower portion has a decreasing diameter toward the lower end.

In any of the embodiments, the at least one seal band may be formed from a polymeric material and the outer surface of the liner body is defined by a textile cover. The at least one seal band extends through the textile cover and interlocks therewith. Locating indicia may be provided between each of the seal bands.

In a method for placing a seal component on a suspension liner and securing therewith, the method may include the steps of: providing a liner having a liner body forming an axis and having an outer surface including a plurality of seal bands located along the height of the liner body and an outer surface of the liner body; placing a seal component having open upper and lower ends defining an opening therethrough and an internal surface having an axis arranged concentric with the axis over the liner; and securing the seal component to the liner body by frictionally engaging the internal surface with at least one of the plurality of seal bands.

BRIEF DESCRIPTION OF THE DRAWINGS

The numerous other advantages, features and functions of embodiments of a suspension liner will become readily apparent and better understood in view of the following description and accompanying drawings. The following description is not intended to limit the scope of the suspension liner, but instead merely provides exemplary embodiments for ease of understanding.

FIG. 3 is a detailed view showing concentric seal bands disposed about an outer cover of the liner body.

FIG. 4 is a detailed view showing a spiral configuration of seal bands disposed about an outer cover of the liner body.

FIGS. 5a and 5b are schematic views showing various surface textures of a liner body.

FIG. 10 is a cross-section of another seal component having a plurality of fins.

FIGS. 11 and 12 are schematic views showing a seal component having a folding structure.

FIG. 24A is an elevational view of the suspension liner of FIG. 23A with the seal component of FIG. 21.

FIG. 24B is a detail view taken from XXIV B in FIG. 24A.

FIG. 24C is a detail view taken from XXIV C in FIG. 24A.

FIG. 27 is an elevational view of a seal component having a textile portion.

FIG. 28A is an elevational view of the suspension liner of FIG. 23A with the seal component of FIG. 27.

FIG. 28B is a detail view taken from XXVIII A in FIG. 28A.

FIG. 29A is a sectional view taken along line XXIX A-XXIX A in FIG. 27.

FIG. 29B is a detail view taken from XXIX B in FIG. 29A.

FIG. 30A is a perspective view of another seal component embodiment.

FIG. 30B is a sectional view taken along line XXX B-XXX B in FIG. 30A.

FIGS. 31A-31E show methods for donning the adjustable seal system of FIG. 24A.

FIG. 36A is a detail view showing an interior interface between a sleeve and base of a seal component.

FIG. 36B is a detail taken from XXXVIB in FIG. 36A.

FIG. 36C is a detail view showing an exterior interface between a sleeve and base in a seal component.

FIG. 37 is a schematic sectional view of a variation of a base of a seal component for securing to a sleeve (not shown).

Figure 2:
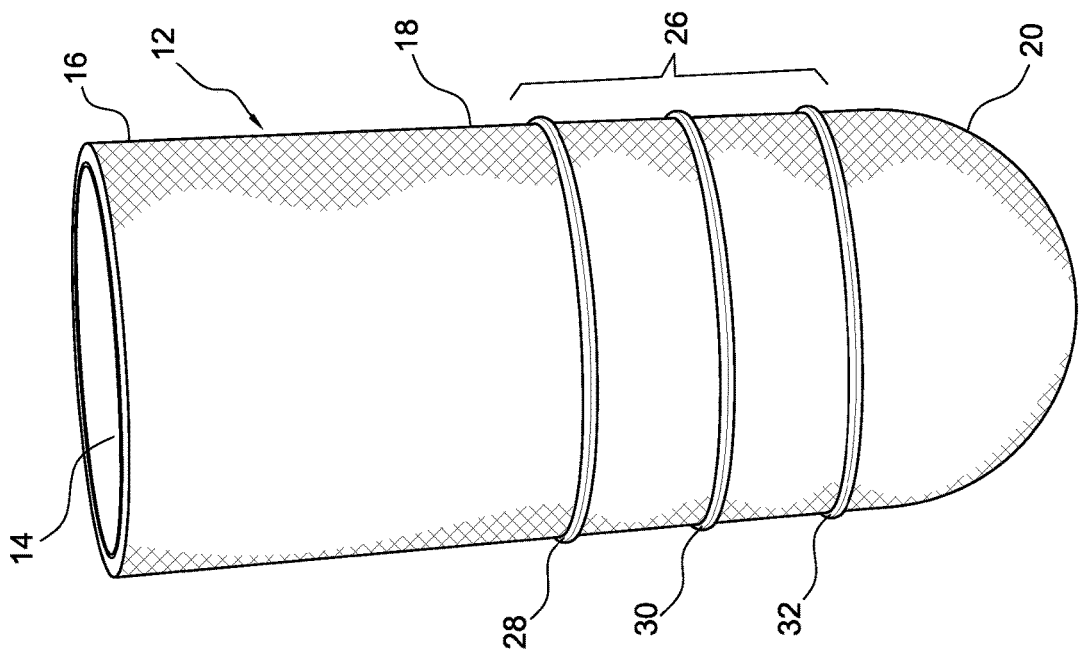
FIG. 2 is a perspective view showing the liner of FIG. 1 without a seal component.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary configurations of a liner, and in no way limit the structures or configurations of a liner thereof according to the present disclosure.

DETAILED DESCRIPTION OF VARIOUS EMBODIMENTS

A better understanding of different embodiments of the invention may be had from the following description read in conjunction with the accompanying drawings in which like reference characters refer to like elements.

A. Overview of Suspension Liner Embodiments

In each of the embodiments discussed herein, the suspension liner is intended for use between a residual limb and a prosthesis, such as a hard socket, and to be air-tight when donned over a residual stump. The internal surface of the liner may be formed of a layer of silicone elastomer, therefore serving as a skin interface.

Silicone is advantageous in that it allows for different levels and softness and strength to be incorporated into the liners of the present application. Moreover, silicone permits the addition of selected supplements, such as petroleum jelly and aloe vera, which improve skin care and comfort. The suspension liner, however, can be constructed from a variety of other materials other than from silicone, and the embodiments herein are not limited to suspension liners formed from silicone.

An elasticity controlling matrix material may be provided on the exterior of the liner, the matrix material preferably being relatively compliant in a radial direction and substantially rigid or inelastic in an axial direction. The matrix material may extend over the distal or external side of the prosthesis, and is advantageous in that it prevents movement of the liner when a prosthesis is worn thereover.

A liner in accordance with this disclosure may be fabricated in a sufficient number of sizes to accommodate various sizes of residual limbs. In use, a liner of the type described herein is rolled up from the proximal to the distal end, placed over the distal end of the residual stump and rolled back up or "donned" over the stump like a stocking. This procedure and the benefits achieved thereby are described in detail in U.S. Pat. No. 4,923,474, granted on May 8, 1990 and incorporated herein by reference. In addition, any of the liners and sleeves mentioned herein may be constructed in the manner prescribed by U.S. Pat. No. 4,923,474.

The embodiments of the suspension liner of the present application may be constructed according to the molding methods described in U.S. Pat. No. 6,485,776, granted on Nov. 26, 2002 and the entirety of which is incorporated herein by reference.

B. Operation of a Seal Component in Combination with a Suspension Liner and Prosthetic Socket As taught in U.S. patent application publication no. 2013/0053982, in use a liner carrying a seal component is worn on a residual limb and stepped into a prosthetic socket. As the residual limb is placed into the socket, the seal component forms an airtight seal with an interior surface of the socket and urges air out of the distal end of the socket through a distally positioned expulsion valve. When it is desired to release the connection between the liner and the socket, the valve is released, and the residual limb can be removed from the socket.

When sealing against a socket, it should be kept in mind that the vacuum is formed between the seal component and the distal end of the socket; no vacuum is created proximal of the socket between the liner and the socket. Depending on configurations of the seal component, the seal component may not completely press against the socket wall, in that only portions of the seal press against the socket wall. For example, seal rings of the seal component may press against the socket wall, but portions between the seal rings may not touch the socket wall.

Pressure is inversely proportional to the suspension force needed, so as to ensure stability and rotational control. The seal component preferably forms a hypobaric sealing membrane that conforms to the shape of the internal socket wall, providing an airtight seal between the suspension liner and the socket. It is often desirable that even pressure exists around the seal component in the connection between the socket and liner. There is preferably firm suspension among the liner, socket and residual limb.

C. Embodiments of Adjustable Seal Systems, Seal Components and Methods for Using the Same In observing the suspension liner embodiment of FIGS. 1 and 2, a liner 10 includes a liner body 12 defining an internal cavity 14 for receiving a residual limb. The liner body 12 preferably has an elongate, generally conical shape, and defines a longitudinal axis A-A along which extend proximal and distal portions 16, 20 spaced apart by a middle portion 18. The liner body 12 may be formed from at least one material segment that is at least radially elastically extensible from a relaxed non-extended condition.

A seal component 22 is secured to an outer surface of the liner body 12 among at least one seal band 26 formed along the outer surface of the liner body. In this embodiment, the at least one seal band 26 defines three seal rings 28, 30, 32 located about a circumference of the middle portion 18. The seal rings may be formed from a frictional material to maintain the seal component 22 on the liner. An example of a frictional material is silicone, however other suitable materials may be used. The seal component 22 frictionally fits against at least one of the seal rings, and can be installed among any one of the seal rings, along the length of the liner body. The seal component 22 can likewise be removed from the liner body and readjusted as considered necessary at a new location.

In this embodiment, the seal component is considered detachable in that it can be removed from liner body with destruction, and adjustable so as to be reappointed on the liner body without any adhesive or permanency. According to a desired height of the seal component, the seal component can be installed among any one or more of the seal rings.

Various advantages are provided by this embodiment over known seal systems. The adjustable seal component can be placed proximally if desired to permit vacuum over the majority of the outer surface of the liner body to maximize suspension potential. The adjustable seal component can be arranged on the liner body outer surface to avoid sensitive areas, for example neuromas or scar tissue, to afford the user more comfort over systems where the seal component is at a fixed location.

The impact of volume fluctuations can be mitigated by placement of the seal component at an ideal location for a given user. For example, moving the seal component toward the proximal end of the liner body may compensate a decrease in volume. Further yet, donning and doffing of the liner is made easier. The liner may be inverted and rolled onto the residual limb without the seal component, and the seal component is only installed after the limb is donned on the residual limb.

Figure 1:
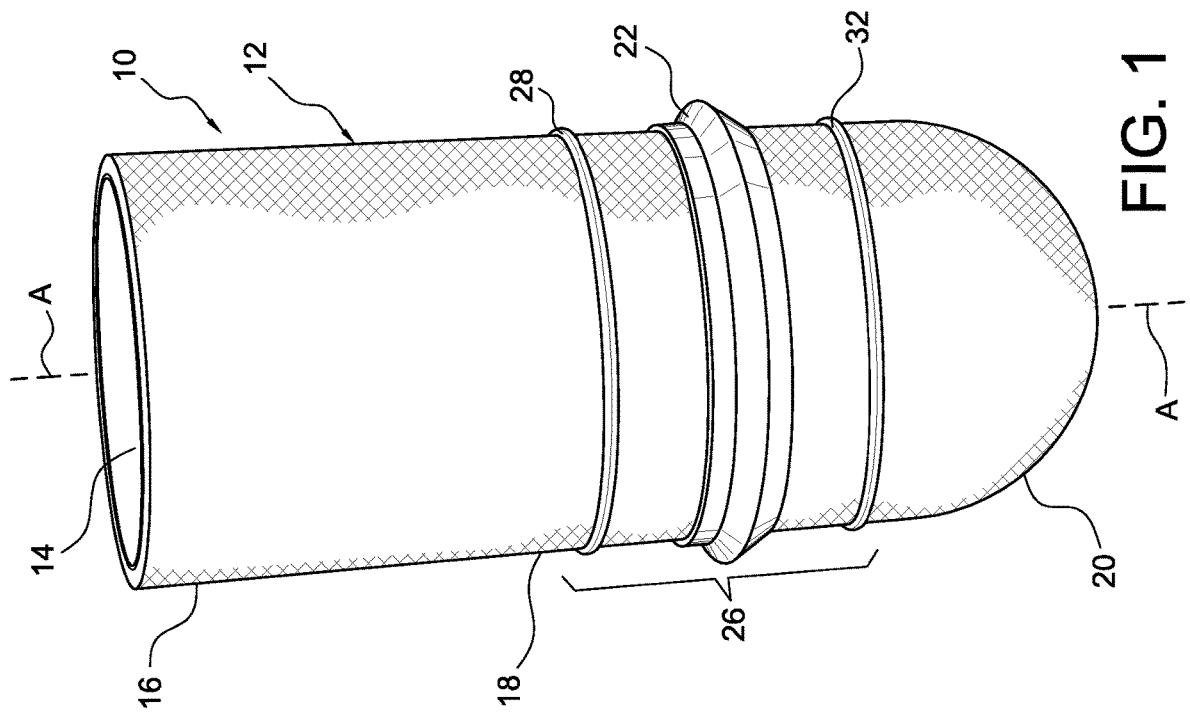
FIG. 1 is a perspective view showing an embodiment of a liner having a movable seal system.

The at least one seal band may take on a variety of configurations and is not limited to the configuration shown in FIGS. 1 and 2. The at least one seal band may be circumferentially segmented over the outer surface, and may take on a variety of thicknesses and shapes.

In an exemplary method of manufacturing the at least one seal band formed from silicone or other polymeric material on a textile-based outer surface or cover, the silicone seal band is formed so as to bleed or wet through the textile and interlock therewith.

Various types of materials may be used to form the at least one seal band. In the disclosed embodiments, a silicone is selected having low viscosity. Various patterns may be formed as the at least one seal band to reduce or eliminate any flow of silicone deposited onto the outer cover. Various yarn types may be selected as a basis in which silicone is encouraged or allowed to wet or bleed through the textile, as well as certain weaves of the textile which facilitate wetting or bleeding of the material forming the at least one seal band.

In observing FIG. 3, a plurality of individual rings 34 extends about the circumference of the liner body 12. Each ring is spaced a distance 36 from one another at specific increments which may be uniform or non-uniform, such as with variable distances. The liner body 12 may also form protruding rings 35, 37 at distal and proximal ends delimiting the plurality of individual rings 34.

FIG. 4 offers a variation of a plurality of rings 38 continuously spiraling along the circumference of the liner body 12. This variation permits rings 38 having different widths and spacing, however each of the rings is continuously formed with another thereby continuously spiraling along the length of the outer cover. Of course, individual rings may be formed, such as in the embodiment of FIG. 3 having different widths, and spacing among one another without necessarily spiraling along the length of the liner body.

The at least one seal band of any of the embodiments may protrude outwardly from the outer cover at various depths, and embodiments may include a plurality of seal bands extending along the entirety of the liner body or only along certain segments. The profile of the at least one seal band may be configured to correspond to an interior portion of the seal component, for example the profile of the at least one seal band may form a profile mating a cavity along the interior surface of the seal component.

In addition to the at least one seal band, various patterns of a frictional material, such as silicone, can be deposited on the outer textile cover to achieve various benefits. One benefit includes rotational control, which is obtained by patterns of the frictional material on the outer cover to minimize rotational movement of the liner relative to the socket. In another benefit, a frictional material may serve to control or fine-tune characteristics of the liner. For example, the addition of silicone rings may serve to decrease radial stretch by inhibiting the stretchability of the outer cover and liner body by being formed from a stiffer material. Alternatively, the rings may provide improved or additional cushioning for stabilizing soft tissue areas in some regions with wider, higher and/or more rings and patterns.

In another variation, the at least one seal band may be colored to provide guidance to the user as to a desirable position of the seal component. For example, if the silicone rings were colored or shaped differently from one another, a user may be able to discern where to locate the seal component. In yet another variation, a matting agent may be used to decrease the coefficient of friction of the at least one seal band to improve donning and doffing of the liner. In yet another variation, the surface texture of the at least one seal band may be configured so the coefficient of friction is adapted to ease donning and doffing of the liner on a user.

The liner may be formed without an outer cover in that the liner body is "naked." In such a naked liner, a matting agent may be used to decrease the coefficient of friction along the outer surface of the liner. The liner body may be formed as a dual durometer, as further explained in U.S. Pat. No. 6,136,039, granted on Oct. 24, 2000 and the entirety of which is incorporated herein by reference.

Surface texturing may be provided on the surface of the liner, as exemplified in FIGS. 5a and 5b. For example, allowing airflow below a seal component to flow across the surface of the liner body and out of a valve. Different textures 40, 42 may be used along the outer surface of the liner body to achieve the necessary airflow.

D. Various Seal Components

Figure 6:
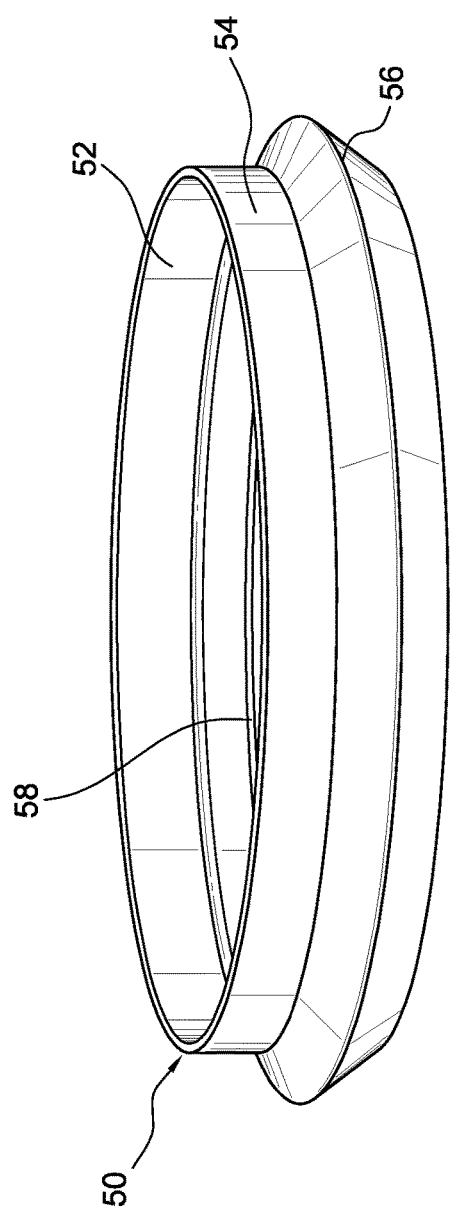
FIG. 6 is a schematic view of a seal component having a single fin.

Referring to FIG. 6, an embodiment of a seal component 50 includes an inner surface 52 arranged to abut a surface of the liner body 12. The seal component 50 defines a ring portion 54 arranged for being flush against the liner body 12 via the inner surface 52. A seal element 56 protrudes outwardly relative to the ring portion 54 and is arranged to flexibly engage the socket. An inner cavity 58 corresponding to seal element 56 permits the seal element 56 to crush or compress inwardly upon donning of the socket. The inner cavity 58 may also mate with at least one seal band of the liner. A ring portion may be provided on both upper and lower sides of the seal element.

Figure 7:
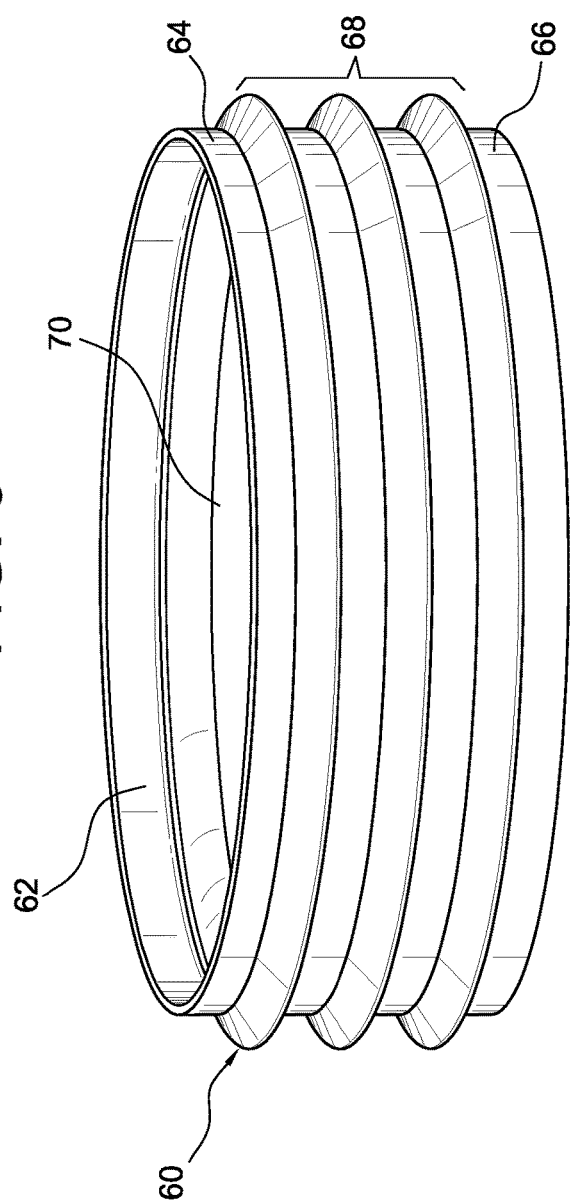
FIG. 7 is a schematic view of a seal component having a plurality of fins.

FIG. 7 shows a seal component 60 similar to the embodiment of FIG. 6 but includes a plurality of seal elements 68. The seal component 60 includes upper and lower ring portions 64, 66 spaced apart by the protruding seal elements 68. The seal component 60 includes an interior surface 62 and inner cavities 70 corresponding to the seal elements 68.

Figure 9:
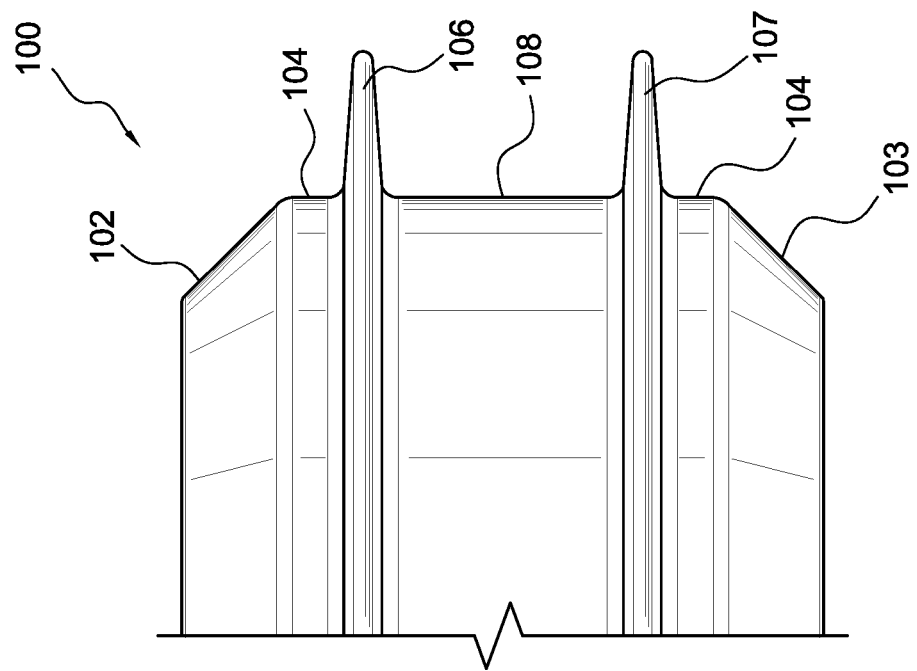
FIG. 9 is a schematic view of a seal component having a plurality of fins.
Figure 8:
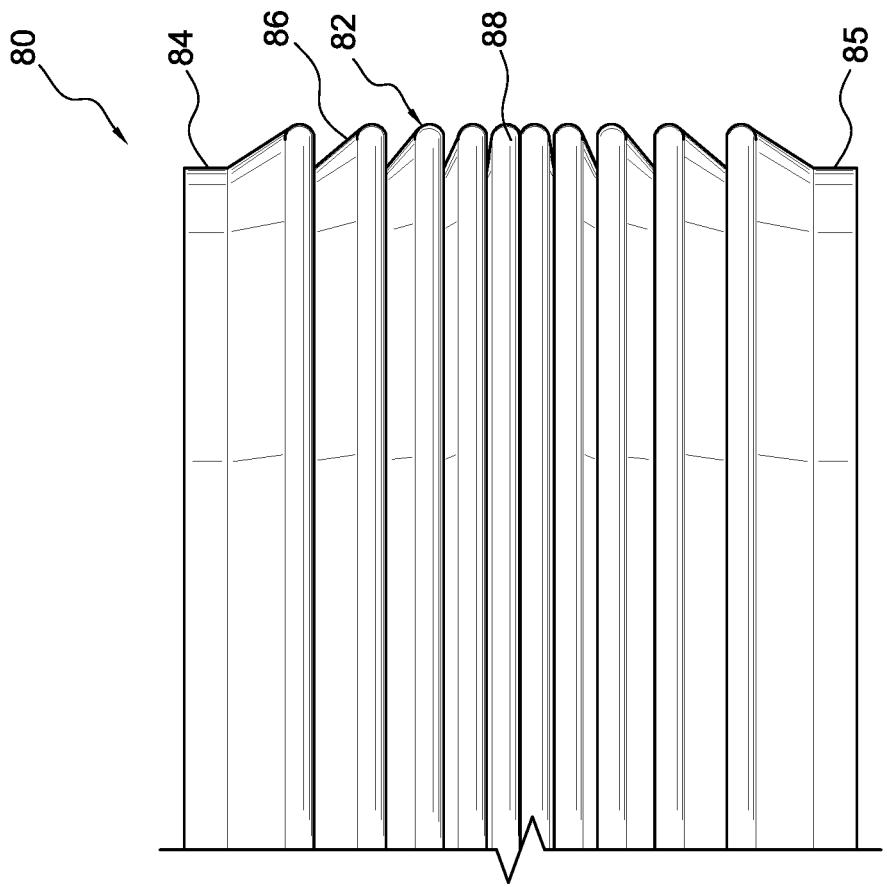
FIG. 8 is a schematic view of a seal component having a plurality of fins.

FIGS. 8 and 9 exemplify embodiments of universal seal components defined in at least a first plane. The seal components are universal in the sense they may be placed onto a liner body in either direction and have end portions generally symmetrical to one another. In other words, it does not matter the orientation the seal component is placed onto the liner body.

FIG. 8 shows seal component 80 having a plurality of seal elements 82 generally concentric with one another. First and second end portions 84, 85 possess mirror image configurations so it does not matter as to which of the first and second end portions 84, 85 is placed on the liner body first and from which direction. A profile 86 of the seal elements 82 may taper toward a substantially flat middle seal element 88 as they span toward the end portions 84, 85 so as to facilitate donning with a socket.

FIG. 9 illustrates a seal component 100 having symmetrical end portions 102, 103 defining a tapered profile for facilitating donning of a socket. The end portions 102, 103 are spaced a distance 104 from seal elements 106, 107 protruding transversely and arranged for engagement with a socket wall. The seal elements 106, 107 are spaced apart from one another by a distance 108.

FIG. 10 exemplifies another seal component 120 that is universal in the sense it does not matter whether or not it is placed onto a liner body from either end direction or inside out. FIG. 10 shows a cross-section of such a seal component in that the seal component 120 has end portions 122 symmetrical with one another, with seal elements 124 protruding gradually more transversely from both sides relative to the width of a seal component 128 until reaching a maximum protruding seal element 126.

FIGS. 11 and 12 show a seal component 140 defining a folding structure. In this seal component 140, there are three concentric rings 142, 144, 146, with the first ring 142 having the greatest circumference and the second and third rings 144, 146 having consecutively less circumferences. Due to the flexibility of the seal component 140, the second and third rings 144, 146 may fold into one another along fold lines 152. The interior of the seal component 140 may include at least one cavity 148 for engaging at least one seal band of the liner body, and may include various protrusions 150 for engaging the liner body.

Figure 13:
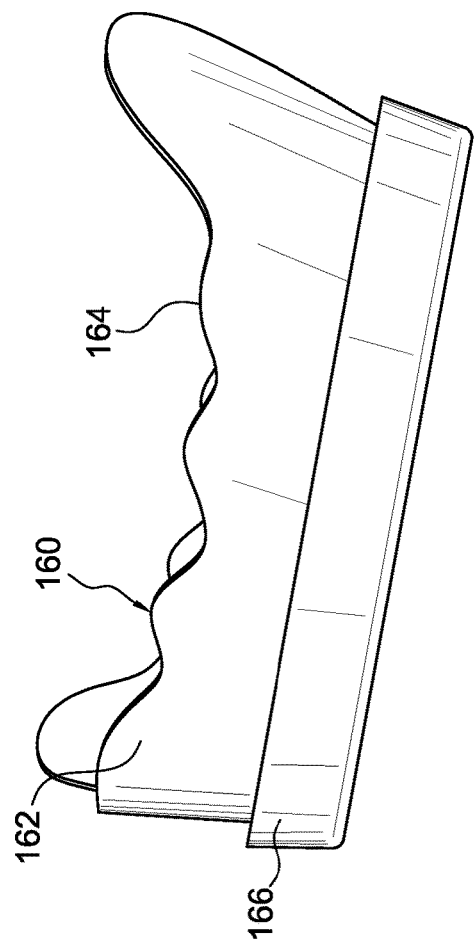
FIGS. 13 and 14 are schematic views showing a seal component having a rippled edge portion.
Figure 14:
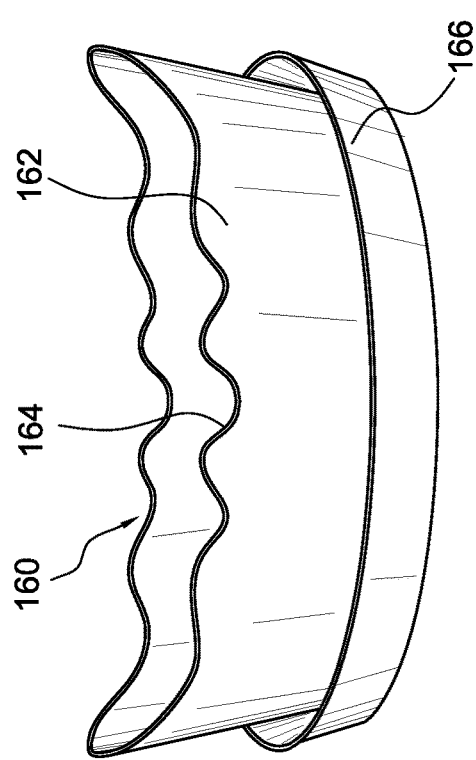

FIGS. 13 and 14 illustrate a seal component 160 having a pressure or tension indicator 164 along an upper portion 162. In this embodiment, the tension indicator 164 is defined as a rippled edge along the upper portion 162 and spaced from a lower seal element 166. When tensioned, as exemplified in FIG. 14, the tension indicator 164 straightens or partially straightens. The tension indicator 164 may indicate if there is excessive or insufficient tension about the seal component 160.

Figure 15:
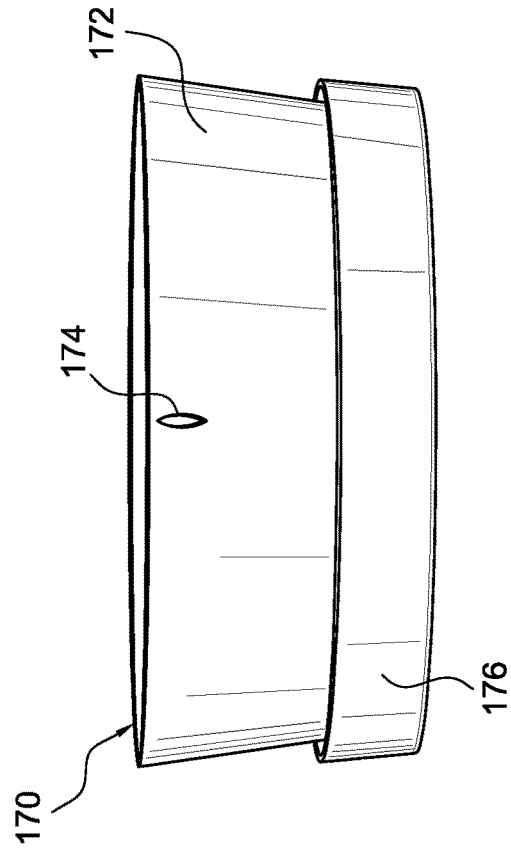
FIGS. 15 and 16 are schematic views showing a seal component having a color indicator.
Figure 16:
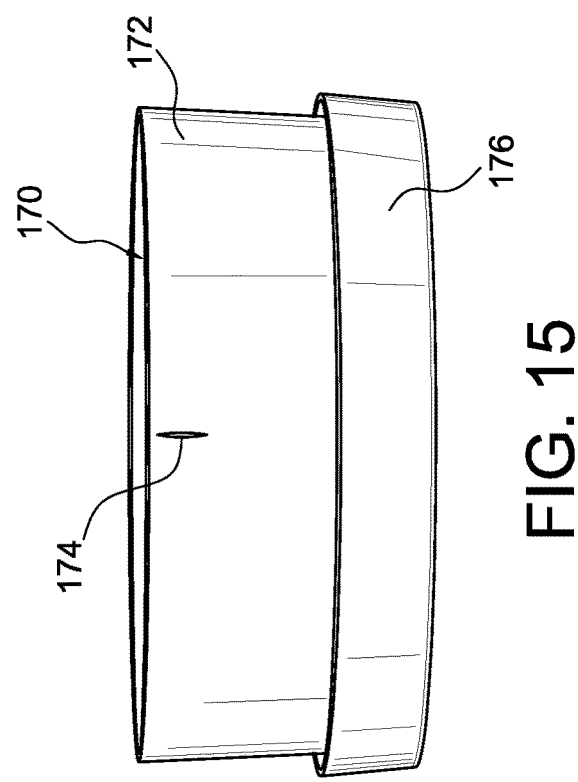

FIGS. 15 and 16 provide a variation of a tension indicator on a seal component 170. In this variation, an upper portion 172 includes a colored recess 174 that opens when the upper portion 172 is tensioned thereby exposing more color that is found in the colored recess 174. A seal element 176 is provided below the colored recess 174.

Figure 18:
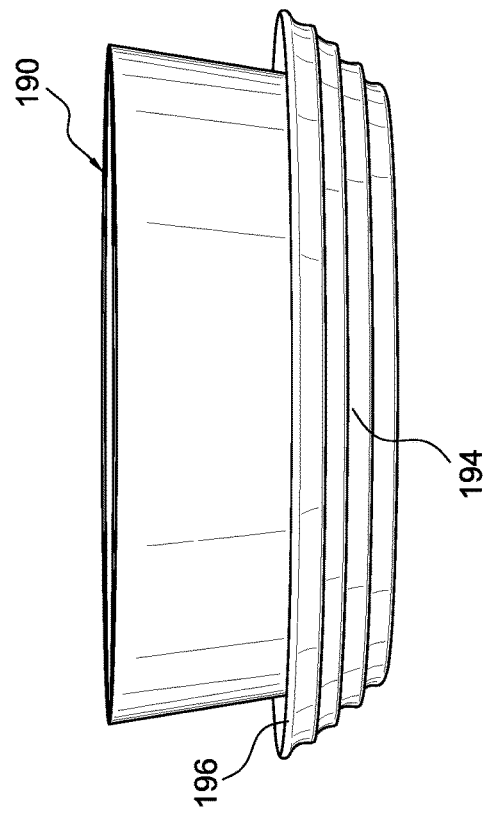
FIG. 18 is a schematic view showing a seal component having a plurality of lower fins.
Figure 17:
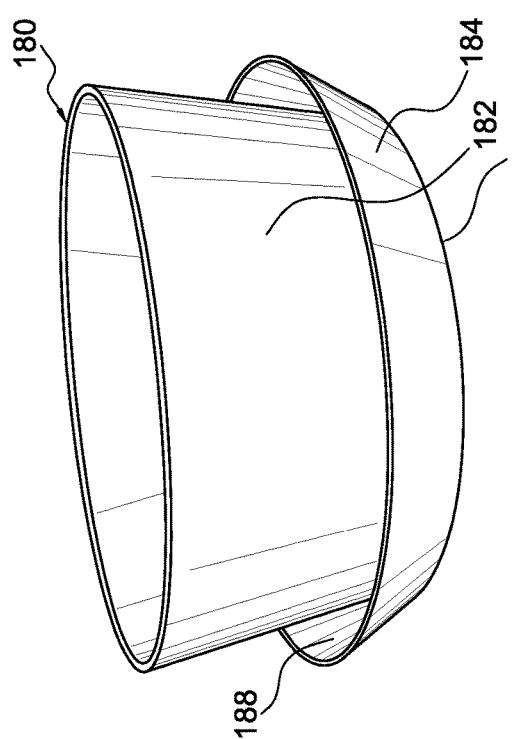
FIG. 17 is a schematic view showing a seal component having a lower fin.

FIGS. 17 and 18 show various seal components having one or multiple seal elements. FIG. 17 depicts a seal component 180 having an elongate portion 182 for extending about a liner body outer surface, and a seal element 184 protruding from a lower end portion 186 of the seal component 180. The seal element 184 extends outwardly from the lower end portion 186 at an angle and forms a tapering width 188 from the elongate portion 182. The seal component 180 is open at both upper and lower ends thereby forming an annular inner surface for securing about a liner body.

FIG. 18 shows a variation of the seal component 180 of FIG. 17 in that the seal component 190 of FIG. 18 includes a plurality of ribs 196 on a seal element 194. A user may employ different seal components or seal sizes for different activities. For example, the seal component of FIG. 18 may be used for more aggressive sealing by way of the multiple ribs 196 whereas the seal component of FIG. 17 may be used for lower activity users.

Figure 20:
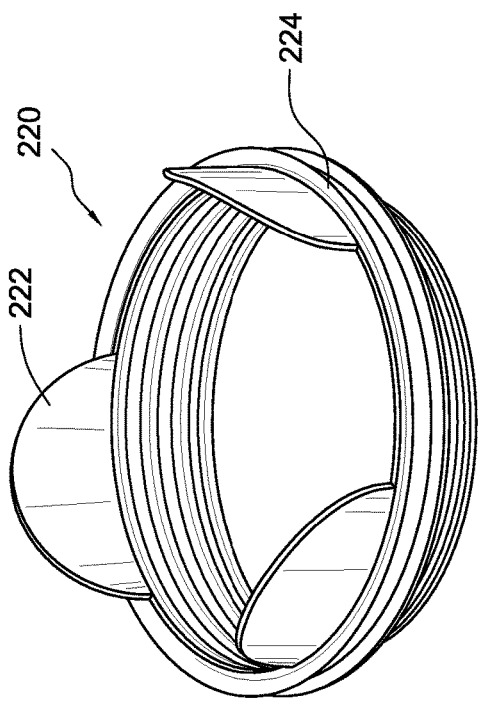
FIG. 20 is a schematic view showing another seal component having a plurality of proximal handles.
Figure 19:
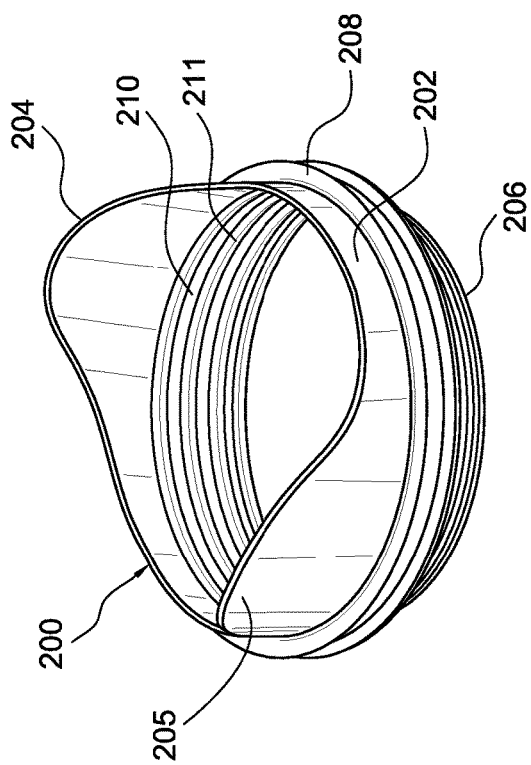
FIG. 19 is a schematic view showing a seal component having a plurality of proximal handles.

Referring to the embodiment of FIGS. 19 and 20, seal components may include handles for donning the seal components onto a liner body after the liner body is already donned on the residual limb of the user.

FIG. 19 exemplifies a seal component 200 having opposed handles 204, 205 that the user can grasp to pull the seal component 200 onto a liner body against any resistance by the liner body cover and an interior surface 210 of the seal component. The interior surface 210 may include a plurality of inner rings 211 that provide resistance and are used to secure against the liner body. The seal component 200 may include an upper portion 202 spacing the handles 204, 205 from a seal element 208. A lower portion 206 extends below the seal element 208 and opens at the bottom of the seal component 200.

FIG. 20 illustrates another embodiment of a seal component 220 having three handles 222 directly extending from a seal element 224. The handles may be constructed from a variety of different materials and may be molded directly with the seal component or adhered, fastened or locked on the liner body. The handles may be permanently fixed or fixed only for the task of donning or doffing of the seal component. The handles may be formed differently from the seal component, and may be formed from a textile or different elastomeric material such as polyurethane.

Figure 21:
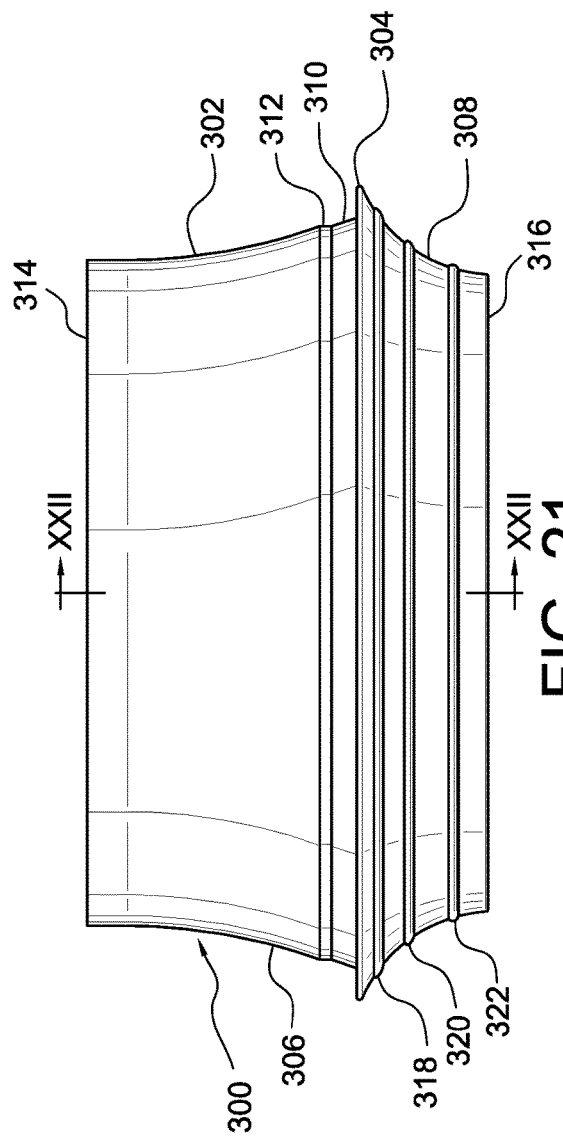
FIG. 21 is an elevational view of another seal component having a collapsible seal.
Figure 22:
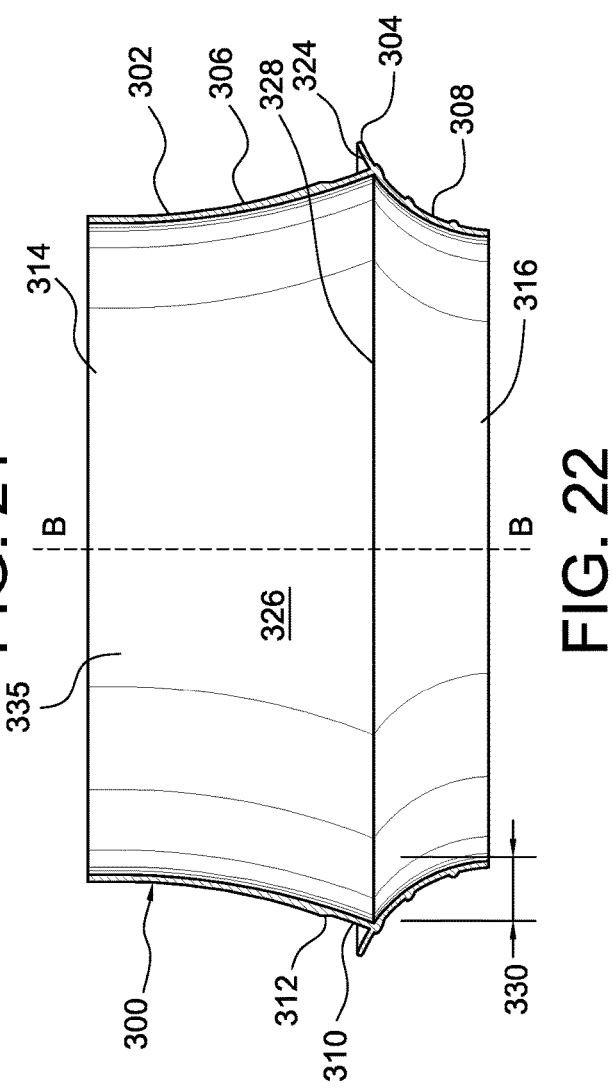
FIG. 22 is a cross-section taken along line XXII-XXII from FIG. 21.
Figure 23B:
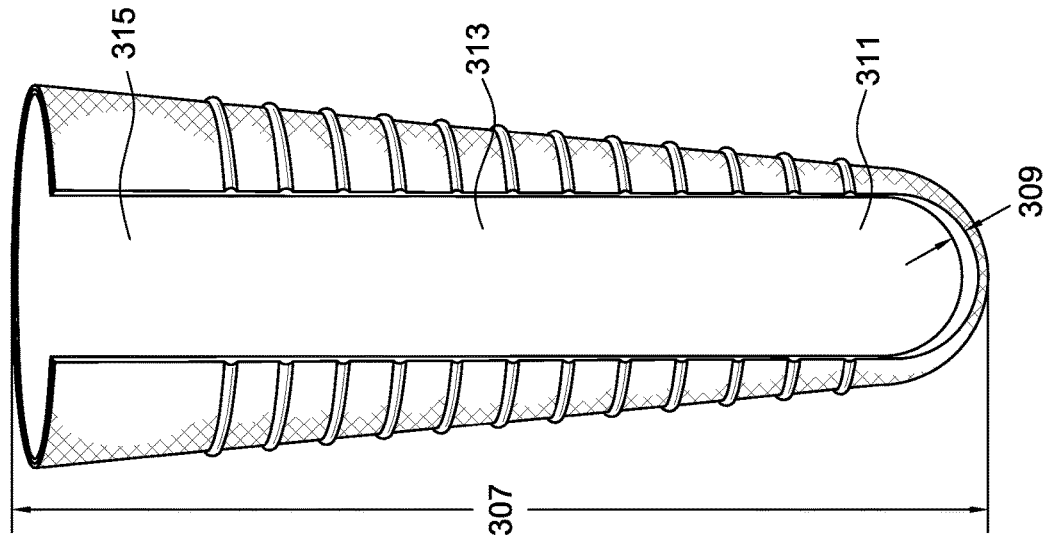
FIG. 23B is an elevational view showing a cross-section taken along line XXIII B-XXIII B.
Figure 23A:
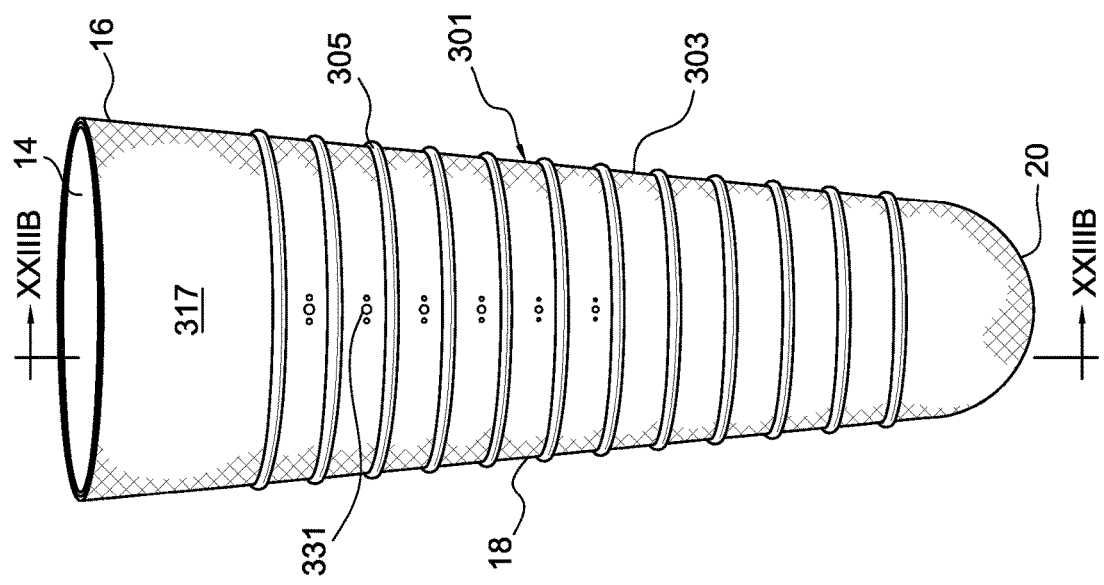
FIG. 23A is an elevational view showing an embodiment of a suspension liner with a plurality of seal bands.

FIGS. 21 and 22 illustrate another seal component 300 having open upper and lower ends 314, 316, and an internal surface 326 for securing over a liner, as depicted in FIG. 23A generally using a liner 301 having the at least one seal band 305. The internal surface 326 is arranged to engage and frictionally secure against the at least one seal band 26 on the liner 10 and forms through an opening 335 between the upper and lower ends 314, 316.

The seal component has an upper portion 302 with a curvature 306 descending to a seal 304, and a lower portion 308 curvingly ascending to the seal 304. The seal 304 extends from the lower portion 308 and extends a distance beyond a periphery of the curvature 306. The upper portion 302 defines a recess 310 formed by the periphery of the curvature 306 proximate the seal 304, and a bevel 312 delimiting a top portion of the recess 310 from the curvature 306.

The lower portion 308 may define a plurality of ribs 318, 320, 322 circumferentially extending around a periphery of the lower portion 308. The ribs 318, 320, 322 are arranged along the height of the lower portion 308 to improve sealing with a socket wall. The ribs 318, 320, 322 may have different cross-sectional shapes, however in the preferred embodiment depicted in FIG. 21, the ribs 318, 320, 322 have a curved cross-section.

The seal 304 is arranged to protrude away from a liner surface a distance 330 when not installed in a socket, and subsequently collapse against the liner surface when placed and engaging a socket, essentially losing the distance 330. The seal 304 forms a flap 324 protruding away from the upper portion 302 a distance while having a base 328 intersecting with the upper curvature 306. The flap 324 generally has a size corresponding to the recess 310 such that upon insertion into a socket, the flap 324 is urged into the recess 310, and has an end portion that may abut the bevel 312. The upper and lower portions 302, 308 generally intersect at a base 328 of the flap 324.

Returning to FIG. 23A, the liner 301 has a liner body 303 in the shape of a conical liner forming an axis A-A and having an outer surface 317. The liner body 303 may be formed similarly to the suspension liners of FIGS. 1-4. The outer surface 317 includes a plurality of seal bands 305 located along the height 307 of the liner body 303 and an outer surface 317 of the liner body 303. The outer surface 317 may include indicia 331 between or at each of the seal bands to advise the user where a recommended seal component 300 placement may be located.

FIG. 23B discloses a cross-section of the suspension liner 300 of FIG. 23A wherein the distal end defines a greatest thickness of the liner at a location 307 (such as 9 mm). The thickness tapers from the distal portion with a thickness at a location 311 (such 7 mm approaching the middle portion), a thinner thickness at a middle location 313, (such as 3.2 mm) and a thinnest thickness at a proximal end at a location 315 (such as 2.5 mm).

FIGS. 24A-24C disclose the liner 301 of FIG. 23A and detail how the seal component 300 of FIG. 21 secures to the liner and how the seal bands 305 are formed.

Referring to FIG. 24B, seal bands 319, 321, 323, 325 are provided along the outer surface 317 of the liner body 303. The seal component 300 preferably extends over at least one of the seal bands 319, 321, 323, 325, wherein the example of FIG. 24B shows the seal component 300 as extending over two seal bands 319, 321. The seal bands 323, 325 outside the seal component 300 are proximate the upper and lower ends 314, 316 of the seal component 300. It is preferred to place the seal 304 proximate at least one of the seal bands 319, 321, 323, 325 since it is a location requiring firm engagement with the outer surface 317 of the liner body.

The seal component 300 may be configured and dimensioned to assure that it extends over at least two of the seal bands 319, 321, 323, 325 over a corresponding liner to assure firm engagement of the seal component against the outer surface 317 of the liner body 303. The seal component 300 is preferably tensioned over the seal bands and the liner over a residual limb such that the diameter of at least the ends of the upper and lower portions 302, 308 are sized short of the diameter of the liner and/or the seal component is stretched over the liner when the liner is worn on a residual limb and tensioned over the liner.

FIG. 24C shows how the seal bands 305 protrude from the outer surface 317 of the liner body. The seal bands 305 may define a variety of shapes such as bubble, dome, arcuate, semi-hemispherical, square, and other available shapes that may be molded over the liner body. FIG. 24C depicts a preferred shape defining a bubble or dome shape to facilitate movement of the seal component of the seal bands.

The seal bands 305 are desirably arranged to bleed through a textile cover 327 forming the outer surface 317 of the liner body such that a portion 329 of the seal bands is located within the textile cover 327. The seal bands 305 extend through the textile cover 327 to a polymeric material layer 325 forming an interface to the residual limb of the wearer. The seal bands 305 create an airtight interface between the liner and the seal component 300.

Figure 25B:
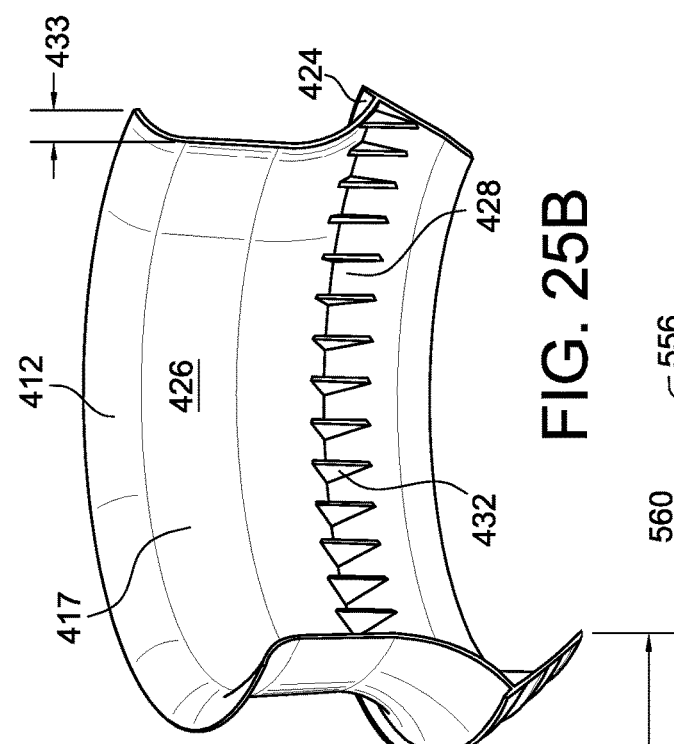
FIG. 25B is a cross-sectional view taken along line XXV-XXV A from FIG. 25A.
Figure 25A:
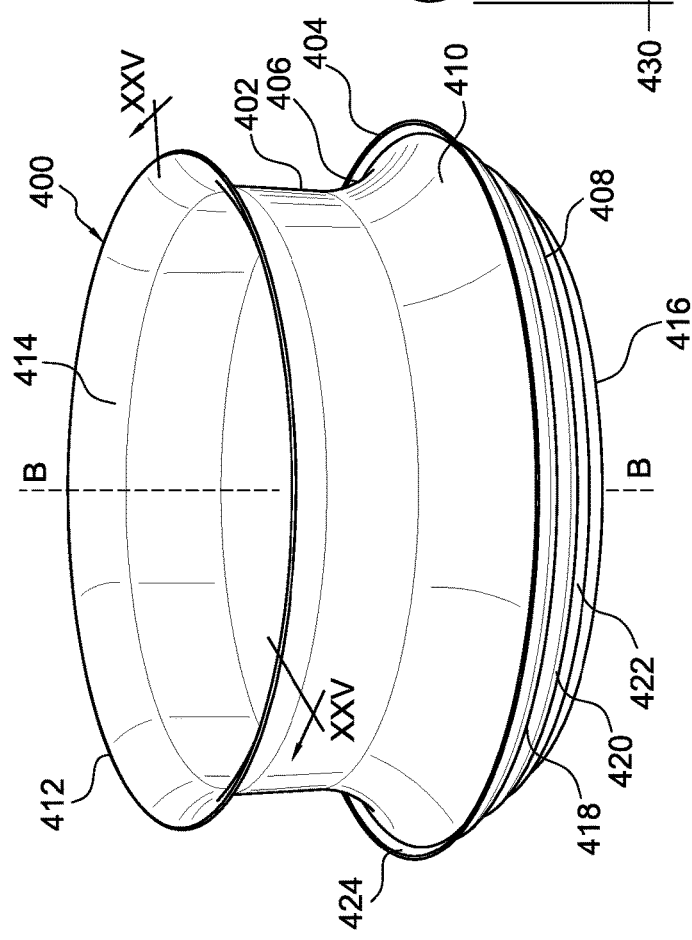
FIG. 25A is perspective view of another seal component having a collapsible seal and interior fins.

FIGS. 25A and 25B exemplify another seal component 400 having open upper and lower ends 414, 416, and an internal surface 426. The seal component 400 can fit onto a liner similarly to the manner of the seal component 300 to the liner 10.

The seal component 400 includes an upper portion 402 having a generally straight profile corresponding to a liner periphery between a brim 412 defined as arcuately extending upwardly away from the axis B-B toward the upper end 414 and a transition portion 406 defined as arcuately extending downwardly away from the axis B-B toward a seal 404. The brim 412 may collapse in part when the liner is inserted into a socket, and extends a distance 433 from the liner wall prior to insertion into a socket.

The seal 404 is located between the upper portion 402 and a lower portion 408 extending upwardly from the lower end 416 and outwardly to the seal 404. The lower portion 408 may have an arcuate cross-section or may extend generally linearly toward the seal 404. The lower portion 408 may define a plurality of ribs 418, 420, 422 circumferentially extending around the periphery of the lower portion 408, and may be arranged similarly to the ribs in the seal component 300.

The seal 404 is formed as a flap 424 extending generally upwardly from a profile of the lower portion 408, and at a junction 428 of the transition portion 406 and the lower portion 408. The transition portion 406 defines a collapsing region 410 adapted to extend from a liner periphery a distance 430 prior to insertion of the liner in a socket. The interior surface 426 of the collapsing region 410 is generally arranged to collapse against an outer wall of a liner when the liner is inserted into a socket, and crush against an interior wall of a socket.

The seal component 400 may include interior blades 432 located along the interior surface 426 and corresponding to the seal 404. The interior blades 432 may be arranged obliquely to the axis B-B, and arranged to collapse against a liner exterior wall. The interior blades 432 may also reinforce the seal 404 to provide a stronger interface between the interior socket wall and the liner. The interior blades 432 may increase the interface between the interior portion of the seal 404 against the liner when collapsed in a socket.

The interior blades 432 are arranged to compensate for volume changes in the residual limb, by expanding and exerting pressure against an interior surface of the socket so as to improve suspension of the liner over known suspension liners with seals.

The interior blades 432 are preferably arranged obliquely to the axis B-B, and this arrangement permits the interior blades 432 to expand outwardly as the liner is donned onto the residual limb and fold down toward the seal wall with the possibility of some overlap over each of the interior blades 432 as the liner is doffed. The interior blades 432 are at an angle so as to ensure that each of the interior blades 432 folds in a proper predetermined direction so as to avoid the creation of any pressure points.

The interior blades 432 are not limited to an obliquely extending configuration but may be arranged in any number of configurations such as either generally parallel or perpendicular relative to the longitudinal axis B-B of the liner.

Figure 26B:
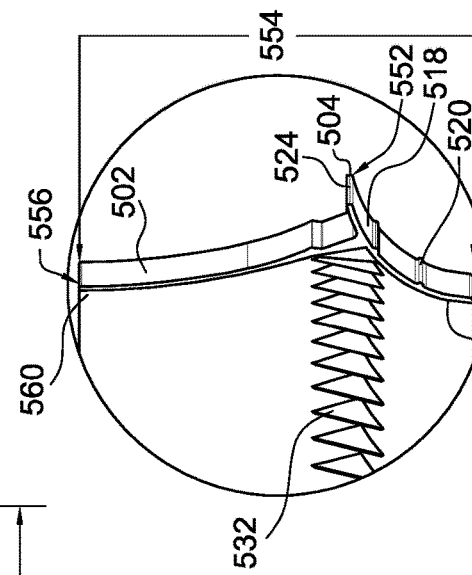
FIG. 26B is a detail view taken from XXVI B in FIG. 26A.
Figure 26A:
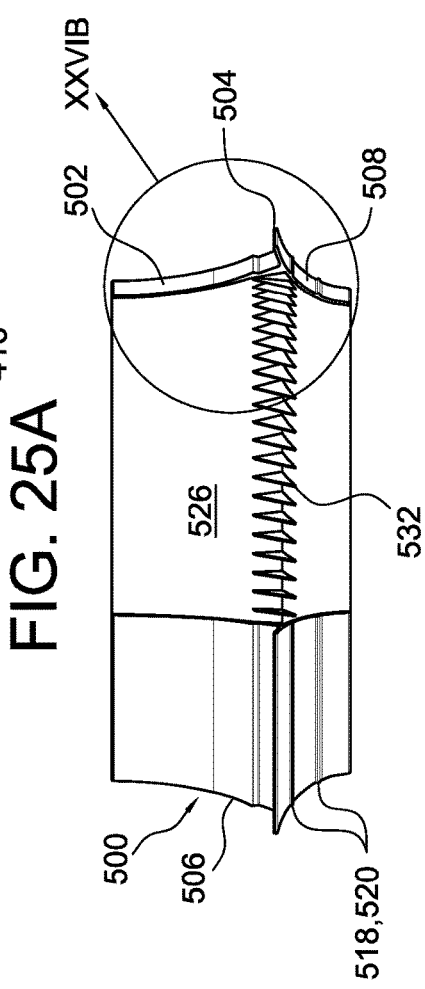
FIG. 26A is a schematic cross-sectional view of a variation of the seal components of FIGS. 21 and 25A.

FIGS. 26A and 26B show a variation of the seal component of FIGS. 21, 22 and 25A. A seal component 500 includes upper, middle and lower portions 502, 506, 508, respectively, with a seal 504 located near or at the middle portion 506. The seal component 500 includes interior blades 532, much arranged in the same manner as in the seal component 400 of FIGS. 25A and 25B. The seal component 500 defines radial seals 518, 520 located below the seal 504, and generally within the lower portion 508.

FIG. 26B exemplifies how the wall thickness of the seal component 500 varies depending on the location. The thickness 550 at the lower portion 508 and the thickness 552 of the seal 504 may be substantially uniform, such as at 1.0 mm, including along the flap 524. The uniform thicknesses 550, 552 may be configured and dimensioned to provide improved strength within the area of the seal and radial seals to assure firm sealing against a socket. The junction of the middle portion 506 and the seal 504 may have an increased thickness 556 to accommodate collapse of the seal or the radial extension of the seal when the seal component is placed in a socket. The upper portion 502 may have a progressively smaller thickness 556 as it approaches a proximal end 560 over a height 554 of the seal component 500.

According to the embodiments of FIGS. 27-29B, an adjustable seal system includes a textile sleeve secured to an upper portion of the seal component and arranged to radially compress against the outer surface of the liner. The textile sleeve is preferably an anatomical conforming fabric. The textile provides an interface for gripping, and thereby minimizing fine hand movements needed to don and adjust the seal component over the liner. The seal component permits retrofitting over existing liners without seal bands for low activity users, thereby enabling a user to decide between whether to use the seal component or a prosthetic sleeve, as taught by example in U.S. Pat. No. 6,592,539, granted Jul. 15, 2003, and incorporated herein by reference, to maintain connection of the liner with a socket.

Seal component 600 has open upper and lower ends defining an opening 617 extending therethrough and an internal surface 626. The seal component 600 has an axis C-C arranged concentric with the axis A-A of the liner body. The internal surface 626 of the seal component is arranged to frictionally engage at least one of the plurality of seal bands 305 and secure on the outer surface 317 of the liner body 303. The adjustable seal system further includes a sleeve 624 secured to the upper end of the seal component 600 and arranged to radially compress against the outer surface 317 of the liner 301. The sleeve 624 is preferably formed from a material different from the seal component 600.

The sleeve 624 is preferably formed from a textile and the seal component 600 is formed from a polymeric material, such as an injection-molded silicone to form the definitive shape of the seal component 600. The sleeve 624 is preferably more flexible and elastic than the seal component 600 such that the sleeve 624 retracts to an original size upon release of tension of the sleeve.

The sleeve 624 is preferably configured and dimensioned to securely tension over the liner. The sleeve 624 may have a diameter less than a diameter of the liner body 303 at the distal portion 20 such that the sleeve 624 stretches over and is tensioned when selectively placed over the outer surface 317 of the liner body 303.

As shown in FIGS. 28A and 28B, the seal component 600 defines a body 601 defining an interior surface 626 arranged to span a distance between at least three seal bands 319, 321, 323 of the liner 301 and engage therewith. While not limited to three seal bands 319, 321, 323, and while a single seal band may be envisioned, it is preferable to include at least two seal bands to provide secure attachment regions to assure the seal component 600 does not slip or provide disproportionate engagement of the seal bands.

The height of the seal component may be sized and configured to extend and engage with any number of seal bands, and the sleeve 624 may extend over at least one seal band 325, however due to the lesser rigidity, the seal component 600 primarily retains the seal component on the liner body with the exception of the radial compression of the sleeve over the outer surface of the liner body.

The seal component 600 includes a seal 604 located below an upper portion 602 and above a lower portion 608, and generally at a middle portion 606. The upper portion is concentric with the liner body 301 and the seal 604 protrudes radially outwardly from the axis C-C relative to the upper portion 602. The seal 604 has a radially outermost portion or seal lip 615 arranged generally concentric with the upper portion 602.

The seal 604 has a lower segment extending outwardly from the lower portion 608 to the seal lip 615. The seal 604 has an upper segment 613 extending inwardly from the seal lip 615 toward the upper portion 602. A clearance 610 is defined between the upper portion 602 and the upper segment 613 such that the seal 604 is arranged to be compressed against the upper portion 602. The seal 604 defines a flap 612 extending from the upper segment 613, and arranged generally parallel with the upper portion 602 and is spaced from the upper portion 602 by the clearance 610.

The lower segment 623 extends outwardly from the lower portion 608 to the seal lip 615 and at least one radial seal 618, 620, and preferably at least two radial seals, projecting outwardly from the lower segment 623. The seal lip 615 and the radial seals 618, 620 are arranged to maintain connection with the inner socket wall, thereby creating a distal vacuum chamber.

The seal component 600 may have a lower portion 608 defining a bottom edge with a curvature 621 and an upper portion 602 having a substantially uniform diameter along its height. The lower portion 608 may have a decreasing diameter toward the lower end, and is arranged to be compressed against the liner when the seal component 600 is donned thereon. The curvature at the bottom edge may be undersized to minimize movement of the seal component 600 when donning the socket.

The sleeve 624 may include at least one material section, and the example of FIGS. 27 and 29A show the sleeve 624 as including a main portion 625 having a first elasticity, and a top band 627 located at an upper end of the main portion 625 and having a second elasticity. The top band 627 may be sized and dimensioned to allow for being the primary portion of the sleeve 624 pulled by a user when donning the seal component 600 on a liner, although the user may likewise grip the main portion.

In any of the embodiments described herein, the shape of the seal component 600 may be conical or cylindrical to accommodate different residual limb shapes.

Any of the seal components may function by creating an airtight seal with the liner body, and securely bond to the underlying liner due to compressive cohesion of silicone upon silicone. Alternatively, the seal component may be permanently adhered to the liner, or the seal component may be coated with a substance arranged to prevent bonding from occurring.

Figure 32A:
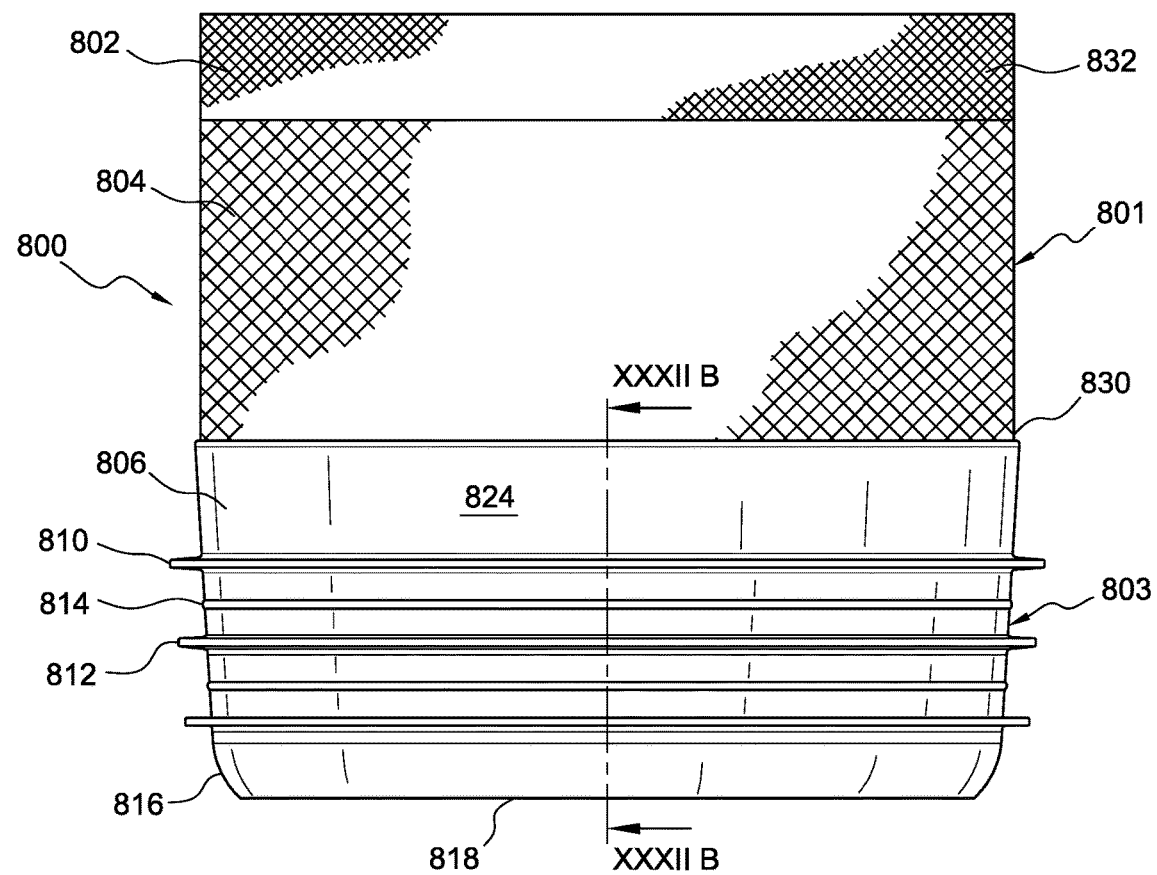
FIG. 32A is an elevational view of another embodiment of a seal component.
Figure 32B:
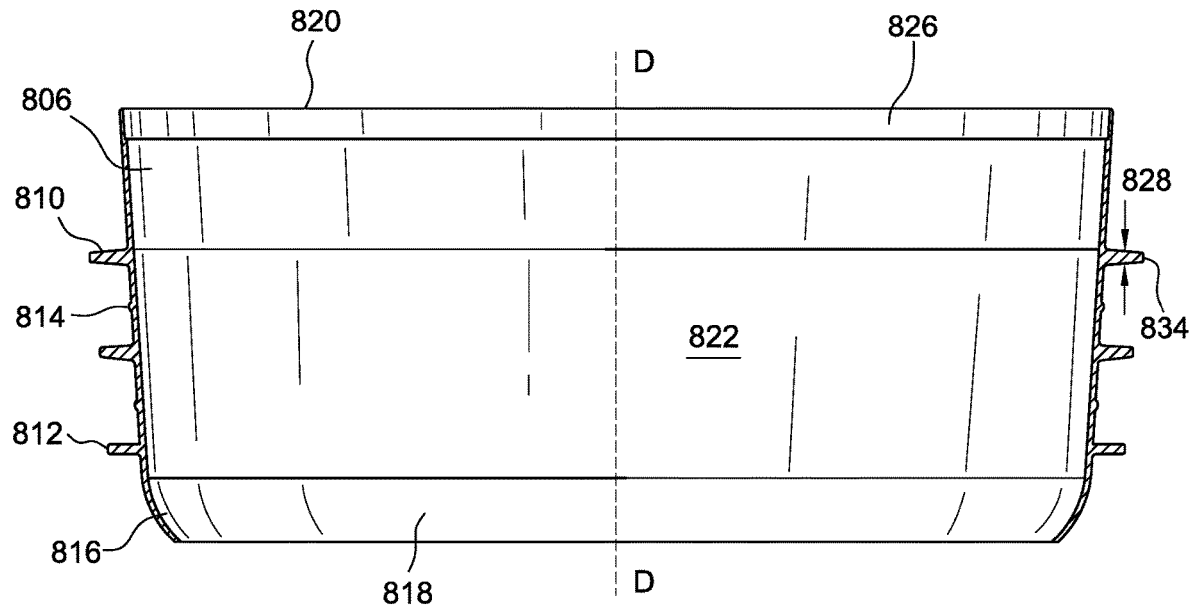
FIG. 32B is a sectional view taken along line XXXII B-XXXII B in FIG. 32A.

FIGS. 32A and 32B exemplify another seal component 800 that may be used with the liner 301 in FIG. 23A having seal bands. The seal component 800 includes a sleeve 801 attached to a body 803 having a plurality of seals 810, 812. The body 803 is integrally secured to the sleeve 801 such that the sleeve 801 and the body 803 are preferably inseparable during donning and doffing of the seal component 800 on a user.

The sleeve 801 may be arranged similarly to the sleeve in FIG. 27, wherein the sleeve 801 includes a top band 802, and a main portion 804. The top band 802 and the main portion 804 may have different elasticities, as described above. The sleeve 801 is tubular and has open opposed ends, with one end 830 securing to the body 803, and another end 832 forming an entry point for drawing the seal component 800 over the liner 301.

The body 803 is monolithically formed in that it is created as a single unitary body, formed from, by example, injection molding. The body may be formed from a single material or composition of materials, but it is preferably unitary in that it is not a composition of individual elements adhered or otherwise secured to one another, but from molding it is generally complete in form.

The body 803 has an upper portion 806 adapted for securing at one end to the sleeve 801 and space the sleeve 801 from the plurality of seals 810, 812, and to further provide structural integrity for the body 803 above the seals 810, 812. The body 803 defines a lower portion 816 that provides structural integrity for the seal component 800, and preferably has a transitional geometry for securing against the liner 301, and may collapse against the liner 301 along with the remainder of the body 803 to better secure against the liner 301.

The body 803 forms open ends 818, 820 about axis D-D, and has inner and outer surfaces 822, 824. The inner surface 822 preferably secures against the entirety of an outer surface of the liner 301, particularly in view of there being a continuous inner surface of the seal component 800 without interruption, such as being devoid of recesses and protrusions, because of the outward profile of the seal component 800 and its components. The body 803 has an interface portion 826 arranged for securing to the end 830 of the sleeve 801. The interface portion 826 is preferably arranged about the end 818 of the body 803, and may be recessed relative to the inner surface 822 of the body 803, such that the combination of the end 830 of the sleeve 801 is flush with the inner surface 822 of the body 803 so as to not create any raised surface relative to the remainder of the inner surface 822 that may create a pressure point.

In this embodiment, the body is arranged to provide enhanced grip between a liner and a socket, by including the plurality of circumferential seals 810, 812. In addition to the circumferential seals 810, 812, at least one rib 814 may be formed between the circumferential seals 810, 812. The at least one rib 814 radially extends less than the radial extension of the circumferential seals 810, 812. The at least one rib 814 is provided to improve sealing with a socket wall, and may be formed similar as in the embodiment of FIGS. 21 and 22. In addition to the degree of radial extension of the plurality of circumferential seals 810, 812 relative to the at least one rib 814, the plurality of circumferential seals 810, 812 have a greater thickness 828 over the at least one rib 814, at a base portion adjacent the outer surface 824. The thickness 828 may taper as the circumferential seals 810, 812 reach a distal tip 834.

The seal component 800 is arranged with the plurality of seals to produce an airtight seal as the user steps into a prosthetic socket, as with other of the aforementioned embodiments. The plurality of seals conform to the shape of the residual limb and inside of the socket to create an improved fit that distributes pressure about the plurality of seals and avoids uncomfortable pressure peaks.

Figure 33A:
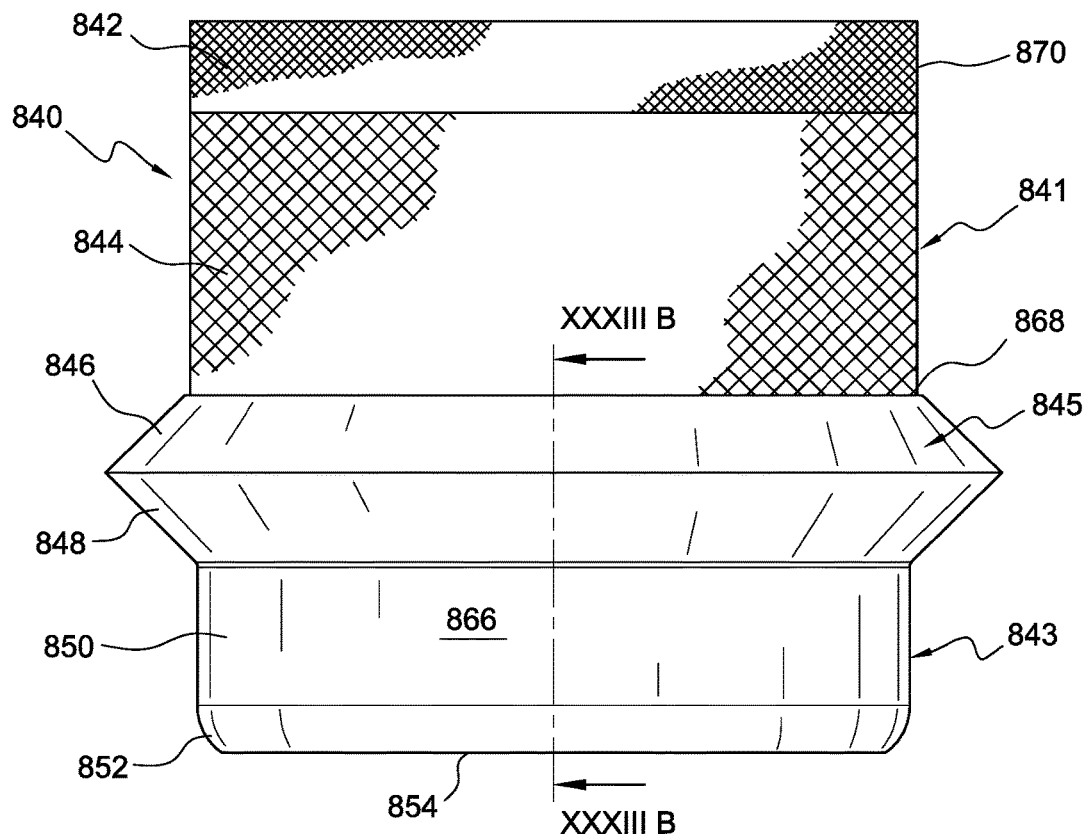
FIG. 33A is an elevational view of another embodiment of a seal component.
Figure 33B:
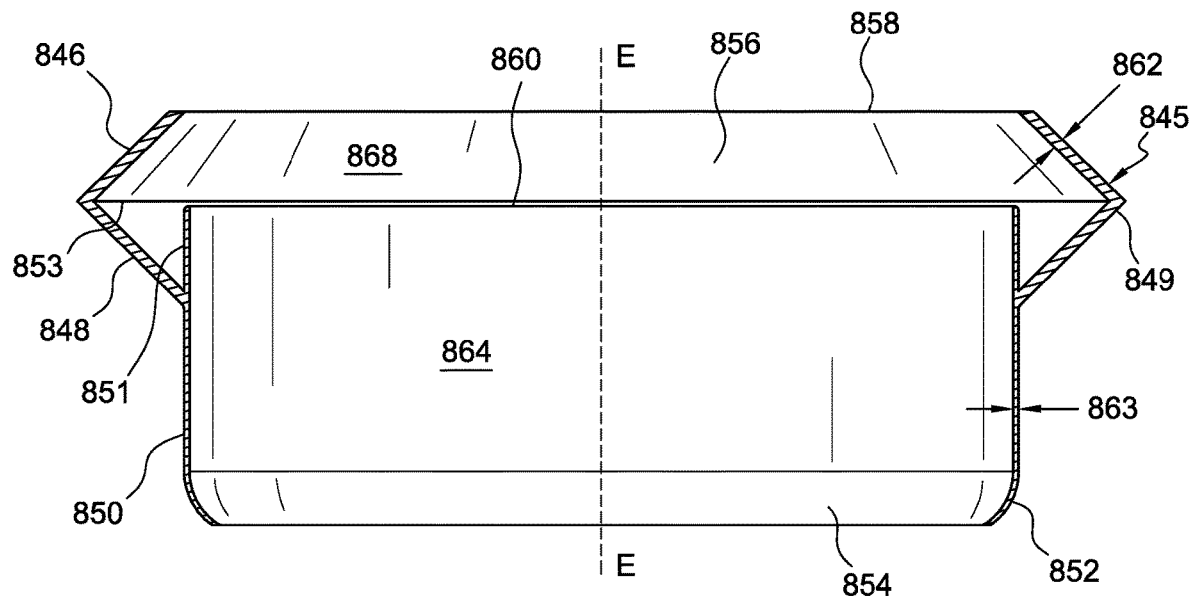
FIG. 33B is a sectional view taken along line XXXIII B-XXXIII B in FIG. 33A.

FIGS. 33A and 33B exemplify yet another seal component 840 that may be used with the liner 301 in FIG. 23A having seal bands. The seal component 840 includes a sleeve 841 attached to a body 843 having a seal 845. The body 843 is integrally secured to the sleeve 841 such that the sleeve 841 and the body 843 are preferably inseparable during donning and doffing of the seal component 840 on a user, as in aforementioned embodiments.

The sleeve 841 may be arranged similarly to the sleeve in FIG. 27, wherein the sleeve 841 includes a top band 842, and a main portion 844. The top band 842 and the main portion 844 may have different elasticities, as described above. The sleeve 841 is tubular and has open opposed ends, with one end 868 securing to the body 843, and another end 870 forming an entry point for drawing the seal component 840 over a liner.

The body 843 defines a lower portion 850 that provides structural integrity for the seal component 840 below the seal 845, and preferably has a transitional geometry 852 at the end portion 854 for securing against the liner, and may collapse against the liner along with the remainder of the body 843 to better secure against the liner. The seal 845 extends upwardly from the lower portion 850, and the seal 845 overlaps an upper portion 851 of the body 843. The upper portion 851 provides structural integrity for the seal component 840, and a lower pitched segment 848 of the seal 845 is adapted to collapse, at least in part, against the upper portion 851, whereas an interior space 868 of an upper pitched segment 846 of the seal 845 is adapted to collapse against the sleeve 841 above a midline 853 of the seal 845, in a non-collapsed condition prior to the seal 845 which corresponds to an upper end of the upper portion 851. The upper portion 851 extends to the midline 853 to assure integrity of the seal 845, and to assure enough surface area of the inner surface 864 to secure against the liner and the corresponding seal bands.

The body 843 forms open ends 854, 856 about axis E-E, and has inner and outer surfaces 864, 866, defined as being located outside the seal 845. The inner surface 854 preferably entirely secures against the liner, whether or not the seal 845 is collapsed. The body 843 has an interface portion 860 arranged for securing to the end 868 of the sleeve 841. The interface portion 860, similar to the embodiment of FIG. 33A, is preferably arranged about the end 868 of the top portion 851, and may be recessed relative to the inner surface 864 of the body 843, such that the combination of the end 868 of the sleeve 841 is flush with the inner surface 864 of the body 843 so as to not create any raised surface relative to the remainder of the inner surface 864 that may create a pressure point, thereby being continuous.

The seal 845 has the upper and lower pitched segments 846, 848 which converge at tip 849. The upper and lower pitched segments 846, 848 may be arranged at a plurality of different angles relative to one another, although the depicted embodiment shows them generally at 90 degrees relative to one another. The pitched segments 846, 848 of the seal 845 form a hypobaric seal, and are arranged to collapse against either the upper portion 851 of the body 843 or the sleeve 841. The pitched segments 846, 848 protrude radially significantly more from the center axis E-E than in some of the aforementioned embodiments since the seal component 840 is arranged to address situations where there is a greater need for more accommodation of volume between the liner and socket. As the seal 845 is adapted to serve as a sealing membrane, thickness 862 may have a greater thickness than thickness 863 of the body 843. Seal 845 has a top edge 858. In view, at least in part, of this arrangement, the seal 845 is durable, and allows radial stretch and comfortable elasticity.

Any other aforementioned seal components may be modified to have lower surface or coefficient of friction. In an example, a gliding surface coating may be deposited on an outer surface of the seal component to assist with donning and doffing the liner with the seal component, so it can slide easily into the socket. Examples of these coatings include Estane or other spray-on, paint or roll-on coatings, that can reduce the coefficient of friction of the surface of the liner. Vapor deposition coatings, such as Parylene and other vapor deposition products, may also be applied to be permanent coatings. In yet another example the coefficient of friction may be reduced or significantly eliminated by using a low friction coating such as Slick Sil® LSR, sold by Surface Solutions Group LLC, of Chicago Ill.

In another variation, the at least one seal band may be colored to provide guidance to the user as to a desirable position of the seal component. For example, if the silicone rings were colored or shaped differently from one another, a user may be able to discern where to locate the seal component. In yet another variation, a matting agent may be used to decrease the coefficient of friction of the at least one seal band to improve donning and doffing of the liner. An example of using a matting agent to reduce the coefficient of friction is discussed in U.S. patent application publication no. 2008/0188949, published Aug. 7, 2008, and incorporated herein by reference.

In yet another variation, the surface texture of the at least one seal band may be configured so the coefficient of friction is adapted to ease donning and doffing of the liner on a user. FIGS. 34A-35B offer examples of reducing the coefficient by modifying the surface texture of the seal component as a whole, or portions of the seal component.

Figure 34A:
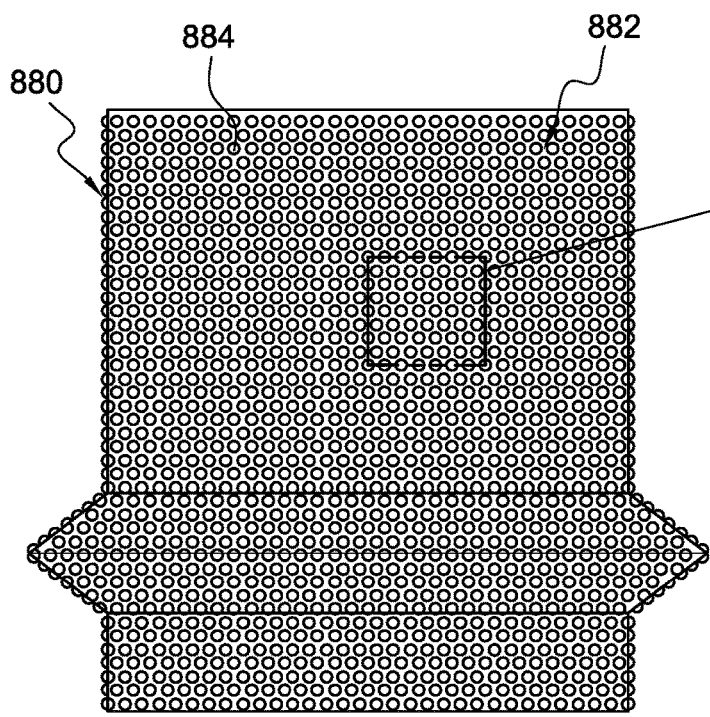
FIG. 34A is an elevational view of another embodiment of a seal component.
Figure 34B:
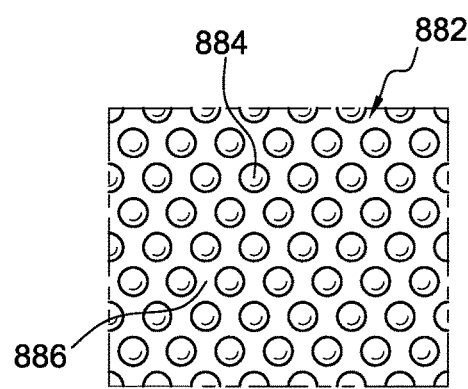
FIG. 34B is a detail view taken from XXXIV B in FIG. 34A.

FIGS. 34A and 34B show a seal component 880 similar to the seal component of FIG. 27. In this example, the entirety of the seal component 880 has a surface texture 882 comprised of distensions 884 spaced apart by indentations 886. The indentations 886 reduce the surface area that slides against an interior wall of the socket, thereby reducing the coefficient of friction of the seal component 880 without the necessity of adding a coating or other materials, such as a matting agent to the material forming the seal component 880. Indeed, the indentations 886 can be formed along at least the outer surface of the seal component 880 when molding the seal component 880, thereby making the seal component 880 with reduced friction in a single manufacturing step, over the coefficient of friction of a seal component 880 without the indentations.

Figure 35A:
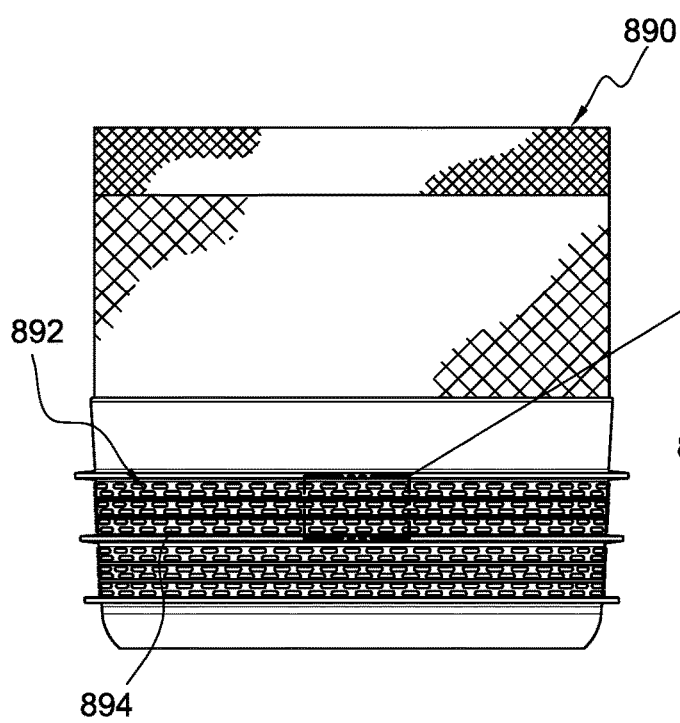
FIG. 35A is an elevational view of another embodiment of a seal component.
Figure 35B:
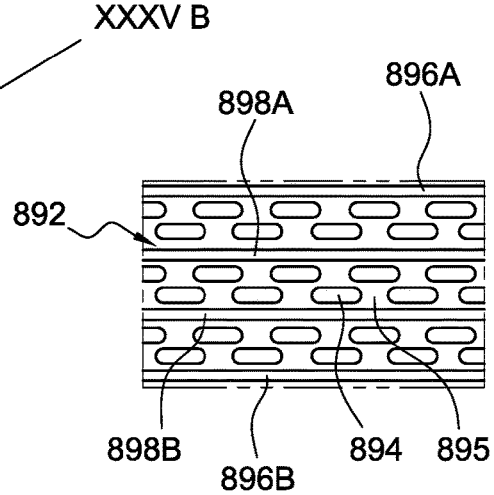
FIG. 35B is a detail view taken from XXXV B in FIG. 35A.

FIGS. 35A and 35B illustrate an example where a discrete section of a seal component 890 has a friction reducing region 892. The seal component 890 bears general similarity to the embodiment of FIG. 32A. The expression "friction reducing region" 892 is meant to convey a region of the seal component 890 that has reduced friction over areas outside the friction reducing region 892, which otherwise both the friction reducing region 892 and the regions outside the friction reducing region 892 would have generally the same coefficient of friction without the modification to the friction reducing region.

In the example of FIGS. 35A and 35B, the friction reducing region 892 is located between a set of first and second circumferential seals 896A, 896B, and among first and second ribs 898A, 898B. The coefficient of friction is reduced by the plurality of protruding bars 894 separated in a pattern, having an elongate form extending circumferentially about the seal component 890, and staggered axially between the first and second circumferential seals 896A, 896B. A recess 895 is formed between and about the bars 894 to reduce the amount of surface area of the seal component 890 that is located between the circumferential seals 896A, 896B, and first and second ribs 898A, 898B.

As shown, the shape and pattern of the bars 894 extend more in the circumferential direction of the seal component 890 to aid in circumferential sealing of the seal component 890 without compromising the ability of the seal component 890 to circumferentially seal against a socket. Although the friction reducing region 892 is not limited by the specific shape and pattern of the friction reducing region 892, the pattern is advantageous in that between each circumferential seal and rib, the bars 894 are juxtaposed and overlap one another in an axial manner. The elongate shape of the bars 894 is advantageous in that they are strengthened in the circumferential direction by having a significantly greater dimension extending in the circumferential direction than in the axial direction, such that a ratio of length (in the circumferential direction) is at least greater than height (in the axial direction), and more preferably at least a ratio of 1:1.5 of height to length.

FIGS. 36A to 36C exemplify an interface 904 of a sleeve 900 to the body or base 902, in another of the aforementioned embodiments. A segment 906 of the sleeve 900 is molded over the base 902 along the interface 904. The sleeve 900 preferably does not extend too deeply along an inner surface 912, and is secured to the base 902 by overmolded material 908 of the base 902, so that the sleeve 900 is integrally secured to the base 902. The overmolding of the base 902 to the sleeve 900 may occur as the base 902 itself is molded, such that the overmolded material 908 is part of the same material comprising the base 902. The overmolded material 908 may be considered an inner wall of the body 902, and the material of the body 902 forming the recess may be considered an outer wall for the purposes of the recess and securing the sleeve thereto.

To assure good adhesion and security of the sleeve 900 to the base 902, the overmolded material 908 may penetrate through textile material forming the sleeve 900 so that at least some of the overmolded material 908 extends through a thickness of the sleeve 900 to meld or combine with the base 902.

FIG. 36B shows how the base 902 may form a peripheral recess 907 about the upper end portion of the base 902. The recess 907 is taken from the inner surface 912 into the thickness 910 of the base 902. As the sleeve 900 has a thickness 918 at least at the segment 906 that is thinner than the thickness 910 of the base 902, the sleeve 900 is preferably flush at the interface with the inner surface 912 of the base 902 so as to minimize any protrusions or recesses, and to assure a generally uniform and continuous inner surface 912 of the base 902. The thickness of the body 902 at the recess 907 may likewise be thicker than the sleeve 900.

FIG. 36C illustrates how the outer side 914 of the base 902 may form a slight ledge 916 about the outer side 914 of the interface due in part to the aforementioned thickness mismatch of the base 902 to the sleeve 900.

FIG. 37 exemplifies a seal component 920 that may be adapted to receive a sleeve (not shown). In this embodiment, the seal component 920 has a continuously formed inner surface 930, as defined in previous examples, and an outer surface 928. The seal component 920 defines a channel or recess 926 bordered by inner and outer walls 922, 924, and circumferentially extending about the axis F-F of the seal component 920.

A sleeve may be provided selectively to the seal component 920 by being inserted into the channel and secured by an adhesive once the seal component 920 is definitively formed. Alternatively, the sleeve may be combined and secured to the seal component 920 during fabrication of the seal component 920, i.e., during molding, whereby material of the seal component 920 at the inner and outer walls 922, 924 extend through a portion of the sleeve located within the channel 926, and interlock with each other and the textile of the sleeve.

FIGS. 30A and 30B show a seal component 700 may be formed as a "donut" type structure. The seal component 700 may have a hollow center 702, to allow for easy donning onto the liner body and enabling the seal component 700 to roll onto the limb. The seal component 700 defines a plurality of radial seals 704 located about the periphery of the outer surface of the seal component 700 so as to provide a plurality of possible radial seals 704 against the or between the outer surface of the liner and the inner surface of the socket.

The radial seals 704 form peaks 706 and ridges 708, arranged not only so the peaks 706 seal against the socket, but the ridges 708 assist the seal component in maintaining its shape as the seal component flattens when donned and pressed against the socket. When the residual limb is inserted onto the socket, the seal component 700 will compress due to the hollow center 702, and create a secure seal via the radial seals 704. The seal component 700 may be formed from a variety of materials, and preferably silicone.

In yet another embodiment, the seal component may be molded directly onto a liner by way of a silicone adhesive or similar elastomeric material that is formed over the liner body. A mold may be provided allowing a clinician to directly mold the seal component to the liner body. The molded seal component may adhere to the liner or may be detachable therewith.

As shown in FIGS. 31A-31E, a method for placing a seal component 300 on a suspension liner 301 and securing therewith includes the steps gripping the top of the suspension liner 301 and sliding over the hand until an inner surface is fully exposed. After exposing as much of the distal end of the suspension liner 301 as possible, the suspension liner 301 is positioned against the residual limb and with light compression roll upward onto the limb. The suspension liner 301 is rolled all the way up the limb. The seal component 300 is pulled over the distal end of the suspension liner 301 after the suspension liner 301 is donned on the limb and is selectively placed over the suspension liner 301 at one of the seal bands. A lubricant spray 321 may be applied to facilitate donning of the suspension liner 301 and the prosthesis. The lubricant is preferably arranged to evaporate quickly after donning to maintain maximum suspension.

In each of the embodiments described herein, the adjustable seal system permits optimal seal placement rather than a fixed seal placement as found in many prior art seal systems. The seal components may be located away from undercuts or shape irregularities defined by a residual limb. The seal height may be decided according to the user's needs, and the seal may be moved to adapt to various volume changes of the residual limb.

The adjustable seal system embodiments require less effort when donning the liner. For example, rather than deal with a permanent seal resisting donning, the liner may be donned and then the seal may be selectively placed along the height of the liner worn by the user.

The adjustable seal embodiments provide improved comfort for the user. The seal height may be decided according to the needs of the user, and sensitive areas may be avoided. The embodiments make it possible to provide temporary relief of pressure below the seal. Because the seal is adjustable, the distal end of the liner may have improved conformability since it does not require being configured with a permanent seal but rather is uninhibited by such structural limitations found in the prior art. For example, the embodiments of the adjustable seal system enable improved proximal support since the liner may be arranged in a longer configuration over prior art liners, and improved proprioception may be obtained since the distal end may be arranged thinner with better linkage to the socket over prior art liners. Due to the seal bands of the liner, there is improved rotational control of the liner and seal relative to the socket.

The adjustable seal embodiments may enable improved durability by having better abrasion resistance due to the versatility in placement of the seal component and its separate yet non-permanent attachment to the liner.

The adjustable seal embodiments reduce pistoning in lower limb prosthetic sockets and allow for more knee flexion during swing phase. The various adjustable seal embodiments are provided to increase the number of patients that can avail themselves of an adjustable seal component with a lower limb prosthetic socket.

While the foregoing embodiments have been described and shown, alternatives and modifications of these embodiments, such as those suggested by others, may be made to fall within the scope of the invention. The principles described may be extended to other types of prosthetic devices.

The invention claimed is:

1. A seal component defining a central axis and forming external and internal surfaces, the seal component having upper and lower ends, the seal component comprising:
   a single unitary body formed from a polymeric material and having an open first end and a second open end defining an opening therethrough and an internal surface about the central axis and an outer surface extending generally parallel and radially spaced from the central axis, the body having a plurality of seals located between the open first and second ends and protruding at least in part radially outward beyond the outer surface and relative to the central axis, the second end of the body defining the lower end of the seal component;
   a textile sleeve having a tubular form and a lower end secured to the open first end of the body, the textile sleeve being formed from an anatomical conforming textile having greater flexibility and elasticity than the body, the textile sleeve axially extending from and beyond the open first end of the body and defining an internal surface about the central axis of the seal component, the textile sleeve including a main portion having a first elasticity, the textile sleeve further having a top band located at an upper end of the main portion and having a second elasticity, the top band defining the upper end of the seal component, the main portion and the top band are radially coextensive with each other;
   wherein the internal surface of the seal component is defined by the body from the second end to the textile sleeve, the textile sleeve defining the internal surface of the seal component from the lower end of textile sleeve to the upper end of the seal component, wherein a segment of the internal surface of the seal component along the textile sleeve is formed from textile and a segment of the internal surface of the seal component along the body is formed from a polymeric material.

2. The seal component of claim 1, wherein the plurality of seals extend circumferentially about the central axis.

3. The seal component of claim 1, wherein the body defines a lower portion and has a transitional geometry arranged toward the central axis.

4. The seal component of claim 3, wherein the lower portion radially extends from the central axis less than the plurality of seals.

5. The seal component of claim 1, wherein the textile sleeve has a thickness less than a thickness of the body located below the textile sleeve.

6. The seal component of claim 1, wherein at least one rib is formed between the plurality of seals.

7. The seal component of claim 6, wherein the at least one rib radially extends less than a radial extension of the plurality of seals.

8. The seal component of claim 7, wherein the plurality of seals have a greater thickness over the at least one rib, at a base portion adjacent the outer surface.

9. The seal component of claim 1, wherein a thickness of the plurality of seals tapers as it reaches a distal tip.

10. The seal component of claim 1, wherein the body defines at least one friction reducing region.

11. The seal component of claim 10, wherein the friction reducing region is defined by a pattern of indentations and protrusions reducing a coefficient of friction of the body relative to a portion of the body without the pattern of indentations and protrusions.

12. The seal component of claim 11, wherein the pattern of indentations and protrusions is arranged to extend circumferentially about the body and the central axis of the body.

13. The seal component of claim 10, wherein the at least one friction reducing region is located outside of the textile sleeve.

14. The seal component of claim 10, wherein an entirety of the body includes the at least one friction reducing region.

15. A seal component comprising:

a single unitary body formed from a polymeric material, the body having an open first end and an open second end defining an opening therethrough and an internal surface about a central axis and an outer surface extending generally parallel and radially spaced from the central axis, the body having at least two seals located between the open first and second ends and protruding at least in part radially outward beyond the outer surface and relative to the central axis, the open first and second ends of the body being devoid of the at least two seals such that the at least two seals radially and circumferentially extend beyond the open first and second ends, the body defining a lower portion having a transitional geometry arranged toward the central axis, the lower portion tapering toward the open second end by radially extending from the central axis less than the at least two seals, the second end of the body defining a lower end of the seal component;

a textile sleeve having a tubular form and secured to the open first end of the body, the textile sleeve having a different elasticity from the body, the textile sleeve axially extending from the open first end of the body, the textile sleeve being formed from an anatomical conforming fabric having greater flexibility and elasticity than the body such that the textile sleeve retracts to an original size upon release of tension of the textile sleeve, the textile sleeve defining an upper end of the seal component.

* * * * *